US012226481B2

(12) United States Patent
Chen et al.

(10) Patent No.: US 12,226,481 B2
(45) Date of Patent: Feb. 18, 2025

(54) CYTOKINE FUSION PROTEINS

(71) Applicant: Beijing Percans Oncology Co., Ltd., Beijing (CN)

(72) Inventors: Yiyou Chen, San Jose, CA (US); Dagang Guo, Beijing (CN)

(73) Assignee: Beijing Percans Oncology Co., Ltd., Beijing (CN)

( * ) Notice: Subject to any disclaimer, the term of this patent is extended or adjusted under 35 U.S.C. 154(b) by 1244 days.

(21) Appl. No.: 16/964,316

(22) PCT Filed: Jan. 24, 2019

(86) PCT No.: PCT/US2019/014985
§ 371 (c)(1),
(2) Date: Oct. 30, 2020

(87) PCT Pub. No.: WO2019/147837
PCT Pub. Date: Aug. 1, 2019

(65) Prior Publication Data
US 2021/0052727 A1   Feb. 25, 2021

(30) Foreign Application Priority Data

Jan. 24, 2018 (WO) ................. PCT/CN2018/073940
Dec. 4, 2018 (WO) ................. PCT/CN2018/119071

(51) Int. Cl.
| | |
|---|---|
| A61K 39/395 | (2006.01) |
| A61K 39/00 | (2006.01) |
| A61K 45/06 | (2006.01) |
| A61P 35/00 | (2006.01) |
| C07K 14/525 | (2006.01) |
| C07K 14/535 | (2006.01) |
| C07K 14/54 | (2006.01) |
| C07K 14/55 | (2006.01) |
| C07K 14/56 | (2006.01) |
| C07K 14/565 | (2006.01) |
| C07K 14/57 | (2006.01) |
| C07K 16/28 | (2006.01) |

(52) U.S. Cl.
CPC .......... *A61K 39/3955* (2013.01); *A61P 35/00* (2018.01); *C07K 14/525* (2013.01); *C07K 14/535* (2013.01); *C07K 14/5418* (2013.01); *C07K 14/5434* (2013.01); *C07K 14/55* (2013.01); *C07K 14/56* (2013.01); *C07K 14/565* (2013.01); *C07K 14/57* (2013.01); *C07K 16/2818* (2013.01); *A61K 2039/585* (2013.01); *A61K 2039/80* (2018.08); *A61K 45/06* (2013.01)

(58) Field of Classification Search
CPC .......... A61K 39/3955; A61K 2039/80; A61K 45/06; A61K 2039/585; A61P 35/00; C07K 14/525; C07K 14/535; C07K 14/5418; C07K 14/5434; C07K 14/55; C07K 14/56; C07K 14/565; C07K 14/57; C07K 16/2818

See application file for complete search history.

(56) References Cited

U.S. PATENT DOCUMENTS

| | | | |
|---|---|---|---|
| 4,518,584 | A | 5/1985 | Mark et al. |
| 4,791,101 | A | 12/1988 | Adolf |
| 2001/0010925 | A1 | 8/2001 | Wiley |
| 2005/0069521 | A1 | 3/2005 | Gillies et al. |
| 2007/0172449 | A1 | 7/2007 | Carmichael et al. |
| 2014/0044675 | A1 | 2/2014 | Hosse et al. |

FOREIGN PATENT DOCUMENTS

| | | | |
|---|---|---|---|
| CN | 1537636 | A | 10/2004 |
| CN | 101166823 | A | 4/2008 |
| CN | 101287748 | A | 10/2008 |
| CN | 101426916 | A | 5/2009 |
| CN | 102906119 | A | 1/2013 |
| CN | 102939303 | A | 2/2013 |
| CN | 106317226 | A | 1/2017 |
| CN | 106795213 | A | 5/2017 |
| CN | 107857818 | A | 3/2018 |
| CN | 108602872 | A | 9/2018 |
| CN | 108883180 | A | 11/2018 |
| JP | 2003507012 | A | 2/2003 |
| WO | WO1985000817 | * | 2/1985 |
| WO | WO-0110912 | A1 | 2/2001 |
| WO | WO 2016/164937 | A2 | 10/2016 |
| WO | WO-2016180715 | A1 * | 11/2016 ......... A61K 47/6813 |
| WO | WO-2017194783 | A1 | 11/2017 |

OTHER PUBLICATIONS

Extended European Search Report dated Oct. 5, 2021 for European Application No. 19743783.3, 15 pages.
Loetscher, H. et al., "Human Tumor Necrosis Factor α (TMFα) Mutants with Exclusive Specificity for the 55-kDa or 75-kDa TNF Receptors," The Journal of Biological Chemistry, vol. 268, No. 35, pp. 26350-26357 (1993).
International Search Report and Written Opinion mailed Oct. 26, 2018 for International Application No. PCT/CN2018/073940, 14 pages.
International Search Report and Written Opinion mailed Sep. 11, 2019 for International Application No. PCT/CN2018/119071, 11 pages.
Invitation to Pay Additional Fees mailed Jun. 26, 2019 for International Application No. PCT/US2019/14985, 2 pages.
International Search Report and Written Opinion mailed Aug. 27, 2019 for International Application No. PCT/US2019/14985, 10 pages.

(Continued)

*Primary Examiner* — Mark Halvorson
*Assistant Examiner* — Dennis J Sullivan
(74) *Attorney, Agent, or Firm* — COOLEY LLP

(57) ABSTRACT

Provided are cytokine fusion proteins comprising a first cytokine fused to a second cytokine, for example, interleukin-2 (IL-2) or interferon-β (IFN-β) fused to the N-terminus of tumor necrosis factor-α (TNF-α), and related compositions and methods of use thereof for treating cancers, either as standalone agents or in combination with autologous tumor vaccines and/or immune checkpoint modulatory agents.

14 Claims, 11 Drawing Sheets

Specification includes a Sequence Listing.

(56) References Cited

OTHER PUBLICATIONS

Korobko, V. G. et al., "Construction and properties of fusion proteins between human interferon-γ and human tumour necrosis factors α and β," Biomedical Science, 2:634-640 (1991).

Liu, L. et al., "Cloning and expression of IL6-TNFA fusion cDNA in *Escherichia coli*," Letters in Biotechnology, vol. 5, No. 4, 1994, pp. 159-162; English language Abstract.

Liu, X. et al., "Co-modification of IL-2-TNFα fusion gene and B7.1 gene to murine breast tumor cells leads to improved tumor rejection and vaccine effect," Chin Med J (Engl), vol. 113, No. 2, pp. 167-171 (2000).

Seno, M. et al., "A hybrid protein between IFN-γ and IL-2," FEBS, 199(2):187-192 (1986).

Zhang, W., Analysis of Mutant Protein and Active Site of Human Tumor Necrosis Factor-α Foreign Medical Sciences (Immunology Section), Dec. 31, 2002, No. 25, vol. 2; English language Abstract.

Zhang, L. L. "Construction, Expression and Activity Determination of Molecular Targeting Drugs," China Dissertation, Sep. 2014, p. 58; English language Abstract.

Zhang, X. F., "Research progress of cytokine fusion proteins," Journal of Medical Molecular Biology (Foreign Medical Sciences), vol. 18, No. 2, Dec. 31, 1996; English language Abstract.

Bartee, E., et al., "Human cancer cells have specifically lost the ability to induce the synergistic state caused by tumor necrosis factor plus interferon-beta," Cytokine, 2009, vol. 47(3), pp. 199-205.

Supplementary Partial European Search Report dated Oct. 5, 2021 for European Application No. 19743783.3, 15 pages.

* cited by examiner

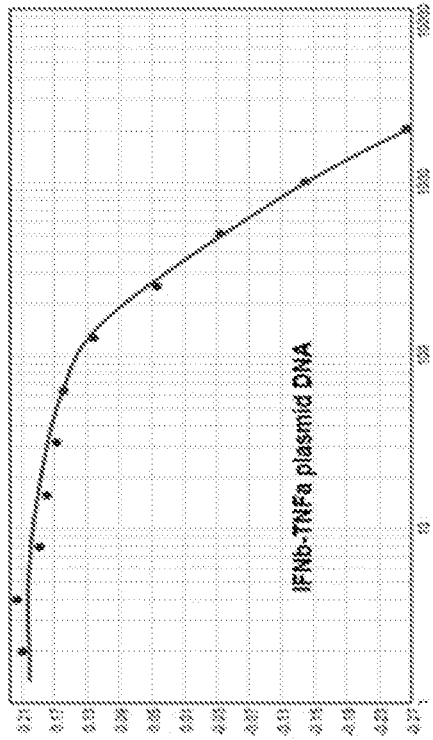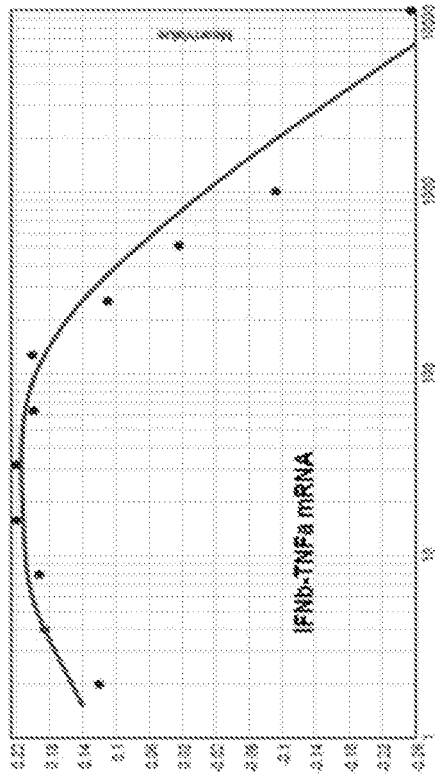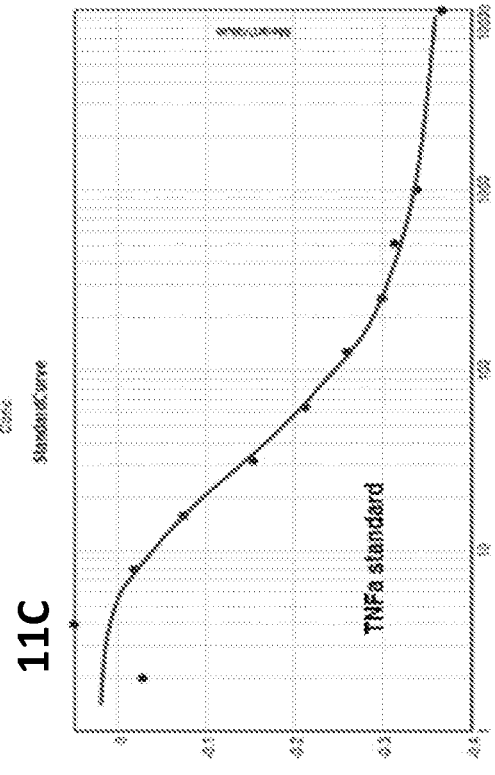
FIGs. 11A-11D

CYTOKINE FUSION PROTEINS

CROSS-REFERENCE TO RELATED APPLICATIONS

This application is a U.S. national stage (§ 371) application of PCT/US2019/014985, filed Jan. 24, 2019, which claims the benefit of Application No. PCT/CN2018/119071, filed Dec. 4, 2018; and Application No. PCT/CN2018/073940, filed Jan. 24, 2018, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BEPE_004_02US_ST25.txt. The text file is 59 KB, was created on Jan. 5, 2023, and is being submitted electronically via Patent Center.

BACKGROUND

Technical Field

The present disclosure relates in part to cytokine fusion proteins comprising a first cytokine fused to a second cytokine, for example, human interleukin-2 (IL-2) or interferon-β (IFN-β) fused to the N-terminus of human tumor necrosis factor-α (TNF-α), and related compositions and methods of use thereof for treating cancers, either as stand-alone agents or in combination with autologous tumor vaccines and/or immune checkpoint modulatory agents.

BRIEF SUMMARY

Embodiments of the present disclosure include cytokine fusion proteins, comprising a first human cytokine fused to the N-terminus of a second human cytokine, wherein the first cytokine differs from the second cytokine and wherein the first and second cytokines are selected from IL-2, TNF-α, IFN-β, IFN-α (for example, IFNA1, IFNA2, IFNA4, IFNA5, IFNA6, IFNA7, IFNA8, IFNA10, IFNA13, IFNA14, IFNA16, IFNA17, IFNA21), IFN-γ, IL-12, GM-CSF, IL-7, IL-23, and IL-27, and optionally wherein the first and second cytokines are separated by a peptide linker. In some embodiments, the amino acid sequence of IL-2, TNF-α, IFN-β, IFN-α, IFN-γ, IL-12, GM-CSF, IL-7, IL-23, and/or IL-27 is selected from Table C1, including fragments and variants thereof having a cytokine signaling activity and/or an anti-tumor activity.

In specific embodiments, the first cytokine is IL-2 or IFN-β and the second cytokine is TNF-α. In some embodiments, the IL-2 comprises, consists, or consists essentially of an amino acid sequence that is at least 90%, 95%, 96%, 97%, 98%, or 99% identical to SEQ ID NO: 1 or 2 or residues 21-153 of SEQ ID NO: 1 or 2 and has a cytokine signaling activity and/or an anti-tumor activity. In some embodiments, the IL-2 comprises a C125S or C125A mutation. In some embodiments, the IFN-β comprises, consists, or consists essentially of an amino acid sequence that is at least 90%, 95%, 96%, 97%, 98%, or 99% identical to SEQ ID NO: 15 and has a cytokine signaling activity and/or an anti-tumor activity.

In some embodiments, the TNF-α comprises, consists, or consists essentially of an amino acid sequence that is at least 90%, 95%, 96%, 97%, 98%, or 99% identical to any of SEQ ID NOs: 3-6 and has a cytokine signaling activity and/or an anti-tumor activity. In some embodiments, the TNF-α comprises at least one mutation which reduces the specific activity of TNF-α by about or at least about 2, 3, 4, 5, 6, 7, 8, 9, 10, 11, or 12-fold, and/or which increases preferential binding to TNFR1 relative to TNFR2, optionally wherein the at least one mutation is selected from S86T, R31E, and R32W, including combinations thereof.

In some embodiments, the fusion protein comprises a peptide linker, optionally a physiologically-stable linker or a releasable linker, optionally a flexible linker or a rigid linker. In some embodiments, the peptide linker is about 1-100 amino acids, about 1-90 amino acids, about 1-80 amino acids, about 1-70 amino acids, about 1-80 amino acids, about 1-50 amino acids, about 1-40 amino acids, about 1-30 amino acids, about 1-20 amino acids, about 1-10 amino acids, or about 1-5 amino acids in length, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 amino acids in length. In some embodiments, the peptide linker is selected from Table L1.

Specific fusion proteins comprise the structure:

```
                                          (SEQ ID NO: 19)
    IL-2(C125S)-(GGGGS)₃-TNF-α (S86T);

(SEQ ID NO: 20)
    IL2(C125A)-(GGGGS)₂-TNF-α (S86T);

(SEQ ID NO: 21)
    IL2(C125A)-(GGGGS)₂-TNF-α (R32W);

(SEQ ID NO: 22)
    IL2(C125A)-PAPAP-TNF-α (S86T);

(SEQ ID NO: 23)
    IL2(C125A)-PAPAP-TNF-α (R32W);

(SEQ ID NO: 24)
    IL2(C125A)-PAEAAAKEAAAKA-TNF-α (S86T);

(SEQ ID NO: 25)
    IL2(C125A)-PAEAAAKEAAAKA-TNF-α (R32W);

IL-2(C125S)-(GGGGS)₃-TNF-α (R31E, S86T);

(SEQ ID NO: 26)
    IFN-β-(GGGGS)₂-TNF-α.
```

In some embodiments, the fusion protein comprises, consists, or consists essentially of an amino acid sequence that is at least 90%, 95%, 96%, 97%, 98%, or 99% identical to a sequence selected from Table F1 and which has a cytokine signaling activity and/or an anti-tumor activity.

Also included are isolated polynucleotides which encodes a fusion protein described herein, an expression vector that comprises the isolated polynucleotide, and/or a host cell that comprises the isolated polynucleotide or the expression vector.

Certain embodiments include therapeutic or vaccine compositions, comprising a fusion protein described herein, and a pharmaceutically-acceptable carrier. Certain embodiments comprise an extended time release formulation. In some embodiments, the extended time release formulation comprises any one or more of poly(lactic-co-glycolic acid) (PLGA), polyethylene glycol (PEG), poly(lactic acid) (PLA), poly(glycolic acid) (PGA), polycaprolactone (PCL), microparticles/microspheres, nanoparticles/nanospheres, and/or liposomes, including any combination thereof. In some embodiments, the extended time release formulation comprises PLGA nanoparticles and/or PLGA-PEG nanoparticles.

Some embodiments comprise an autologous tumor cell vaccine from a subject. In some embodiments, the autologous tumor cell vaccine comprises a whole tumor cell vaccine and/or a cell lysate thereof. In some embodiments, the tumor cell is from a cancer selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer. In some embodiments, the autologous tumor cell vaccine comprises a cancer antigen selected from one or more of human Her2/neu, Her1/EGF receptor (EGFR), Her3, A33 antigen, B7H3, CD5, CD19, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin $\alpha v\beta 3$, integrin $\alpha 5\beta 1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

Certain embodiments comprise at least one immune checkpoint modulatory agent selected from (a) an antagonist of a inhibitory immune checkpoint molecule, and (b) an agonist of a stimulatory immune checkpoint molecule. In some embodiments, the immune checkpoint modulatory agent specifically binds to the immune checkpoint molecule, and is optionally a polypeptide, including an antibody or antigen-binding fragment thereof or a ligand, or a small molecule.

In some embodiments, the inhibitory immune checkpoint molecule is selected from one or more of Programmed Death-Ligand 1 (PD-L1), Programmed Death 1 (PD-1), Programmed Death-Ligand 2 (PD-L2), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, Herpes Virus Entry Mediator (HVEM), and T-cell immunoreceptor with Ig and ITIM domains (TIGIT). In some embodiments, the antagonist of (a) is selected from one or more of:

a PD-L1 and/or PD-L2 antagonist optionally selected from one or more of an antibody or antigen-binding fragment or small molecule that specifically binds thereto, atezolizumab (MPDL3280A), avelumab (MSB0010718C), and durvalumab (MEDI4736);

a PD-1 antagonist optionally selected from one or more of an antibody or antigen-binding fragment or small molecule that specifically binds thereto, nivolumab, pembrolizumab, MK-3475, AMP-224, AMP-514, PDR001, and pidilizumab;

a CTLA-4 antagonist optionally selected from one or more of an antibody or antigen-binding fragment or small molecule that specifically binds thereto, ipilimumab, and tremelimumab;

an IDO antagonist optionally selected from one or more of an antibody or antigen-binding fragment or small molecule that specifically binds thereto, indoximod (NLG-8189), 1-methyl-tryptophan (1MT), β-Carboline (norharmane; 9H-pyrido[3,4-b]indole), rosmarinic acid, and epacadostat;

a TDO antagonist optionally selected from one or more of an antibody or antigen-binding fragment or small molecule that specifically binds thereto, 680C91, and LM10;

a TIM-3 antagonist optionally selected from one or more of an antibody or antigen-binding fragment or small molecule that specifically binds thereto;

a LAG-3 antagonist optionally selected from one or more of an antibody or antigen-binding fragment or small molecule that specifically binds thereto, and BMS-986016;

a VISTA antagonist optionally selected from one or more of an antibody or antigen-binding fragment or small molecule that specifically binds thereto;

a BTLA, CD160, and/or HVEM antagonist optionally selected from one or more of an antibody or antigen-binding fragment or small molecule that specifically binds thereto; and a TIGIT antagonist optionally selected from one or more of an antibody or antigen-binding fragment or small molecule that specifically binds thereto.

In some embodiments, the stimulatory immune checkpoint molecule is selected from one or more of OX40, CD40, Glucocorticoid-Induced TNFR Family Related Gene (GITR), CD137 (4-1BB), CD27, CD28, CD226, and Herpes Virus Entry Mediator (HVEM). In some embodiments, the agonist of (b) is selected from one or more of:

an OX40 agonist optionally selected from one or more of an antibody or antigen-binding fragment or small molecule or ligand that specifically binds thereto, OX86, Fc-OX40L, and GSK3174998;

a CD40 agonist optionally selected from one or more of an antibody or antigen-binding fragment or small molecule or ligand that specifically binds thereto, CP-870, 893, dacetuzumab, Chi Lob 7/4, ADC-1013, and rhCD40L;

a GITR agonist optionally selected from one or more of an antibody or antigen-binding fragment or small molecule or ligand that specifically binds thereto, INCAGN01876, DTA-1, and MEDI1873;

a CD137 agonist optionally selected from one or more of an antibody or antigen-binding fragment or small molecule or ligand that specifically binds thereto, utomilumab, and 4-1BB ligand; a CD27 agonist optionally selected from one or more of an antibody or antigen-binding fragment or small molecule or ligand that specifically binds thereto, varlilumab, and CDX-1127 (1F5);

a CD28 agonist optionally selected from one or more of an antibody or antigen-binding fragment or small molecule or ligand that specifically binds thereto, and TAB08; and an HVEM agonist optionally selected from one or more of an antibody or antigen-binding fragment or small molecule or ligand that specifically binds thereto.

In some embodiments, the therapeutic or vaccine composition described herein for use in treating cancer in a subject in need thereof.

Also included are methods of treating a cancer in a subject in need thereof, comprising administering to the subject a fusion protein described herein, for example, as part of a therapeutic or vaccine composition described herein.

Some embodiments comprise administering the fusion protein to the subject in combination with an Some embodiments comprise administering the fusion protein and the autologous tumor vaccine together in the same therapeutic or vaccine composition, optionally as described herein.

Some embodiments comprise administering the fusion protein to the subject in combination with an immune checkpoint modulatory agent. Some embodiments comprise administering the fusion protein and the immune checkpoint modulatory agent together in the same therapeutic or vaccine composition, optionally as described herein.

Some embodiments comprise administering the fusion protein to the subject in combination with an autologous tumor vaccine and an immune checkpoint modulatory agent.

Some embodiments comprise administering the fusion protein, the autologous tumor vaccine, and the immune checkpoint modulatory agent together in the same therapeutic or vaccine composition, optionally as described herein.

In some embodiments, the cancer is a primary cancer. In some embodiments, the cancer is a metastatic cancer. In some embodiments, the cancer is selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer.

In some embodiments, the metastatic cancer is selected from one or more of:

(a) a bladder cancer which has metastasized to the bone, liver, and/or lungs;
(b) a breast cancer which has metastasized to the bone, brain, liver, and/or lungs;
(c) a colorectal cancer which has metastasized to the liver, lungs, and/or peritoneum;
(d) a kidney cancer which has metastasized to the adrenal glands, bone, brain, liver, and/or lungs;
(e) a lung cancer which has metastasized to the adrenal glands, bone, brain, liver, and/or other lung sites;
(f) a melanoma which has metastasized to the bone, brain, liver, lung, and/or skin/muscle;
(g) a ovarian cancer which has metastasized to the liver, lung, and/or peritoneum;
(h) a pancreatic cancer which has metastasized to the liver, lung, and/or peritoneum;
(i) a prostate cancer which has metastasized to the adrenal glands, bone, liver, and/or lungs;
(j) a stomach cancer which has metastasized to the liver, lung, and/or peritoneum;
(l) a thyroid cancer which has metastasized to the bone, liver, and/or lungs; and
(m) a uterine cancer which has metastasized to the bone, liver, lung, peritoneum, and/or vagina.

Some embodiments comprise administering the fusion protein or therapeutic or vaccine composition by subcutaneous, intravenous, intradermal, intra-tumoral, peri-tumoral, or intra-lymph node injection, including any combination thereof.

BRIEF DESCRIPTION OF THE FIGURES

FIG. 2A shows the results for ZKBY04A fusion protein and FIG. 2B shows the results for commercial TNF-α alone.

FIGS. 11A-11D show that the IFN-β-TNF-α fusion protein has TNF-α activity in the CCK8 assay, whether expressed as a secretory fusion protein from HEK293 cells (11A), or transfected directly into L929 cells (11B). The TNF-α standard (11C) and control transfection (11D) are provided for reference.

DETAILED DESCRIPTION

Definitions

Figure 1:
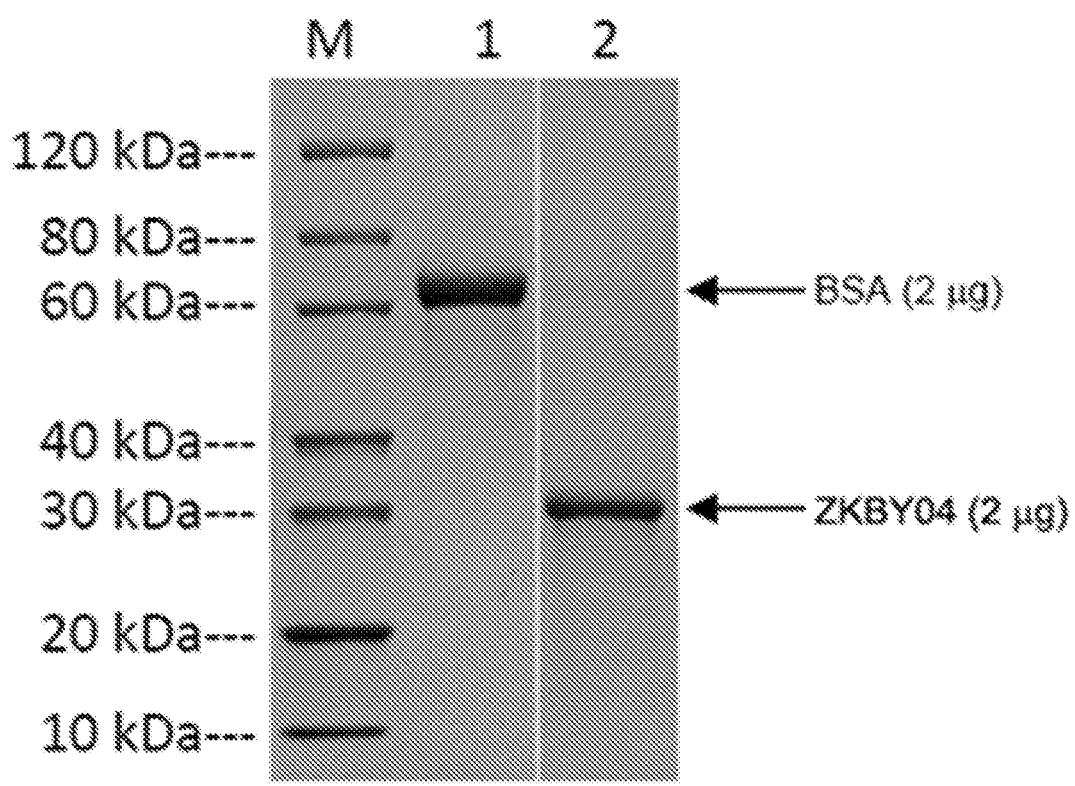
FIG. 1 shows an SDS-PAGE assay for the fusion protein ZKBY04A.

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The practice of the present disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science, Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" includes "one element" and "more than one element" and "at least one element".

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

An "antagonist" refers to biological structure or chemical agent that interferes with or otherwise reduces the physiological action of another agent or molecule. In some instances, the antagonist specifically binds to the other agent or molecule. Included are full and partial antagonists.

An "agonist" refers to biological structure or chemical agent that increases or enhances the physiological action of another agent or molecule. In some instances, the agonist specifically binds to the other agent or molecule. Included are full and partial agonists.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

"Biocompatible" refers to materials or compounds which are generally not injurious to biological functions and which will not result in any degree of unacceptable toxicity, including allergenic and disease states.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise", "comprises", and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "fusion protein" and "fusion polypeptide" are used interchangeably and refer to a polypeptide that is created through the joining of two or more coding sequences, which originally or naturally coded for separate polypeptides; the translation of the joined coding sequences results in a single, fusion polypeptide, typically with structural functional properties derived from each of the separate polypeptides.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as Listeria monocytogenes. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The "half-life" of a polypeptide can refer to the time it takes for the polypeptide to lose half of its pharmacologic, physiologic, or other activity, relative to such activity at the time of administration into the serum or tissue of an organism, or relative to any other defined time-point. "Half-life" can also refer to the time it takes for the amount or concentration of a polypeptide to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts, and is used interchangeably with protein, polypeptide, or peptide. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the enzymes/proteins described herein, or sequences that have deletions from, additions to, and/or substitutions of one or more amino acid of the proteins. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, or may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (for example, a fusion protein) in a composition may be specifically defined. For instance, certain compositions may comprise an agent that is at least 80, 85, 90, 91, 92, 93, 94, 95, 96, 97, 98, 99, or 100% pure, including all decimals and ranges in between, as measured, for example and by no means limiting, by high performance liquid chromatography (HPLC), a well-known form of column chromatography used frequently in biochemistry and analytical chemistry to separate, identify, and quantify compounds. In some instances, the purity of a composition is characterized by the degree of aggregation. For instance, the degree of aggregation of an agent (for example, fusion protein) can be determined by Size-exclusion chromatography (SEC), which separates particles on the basis of size. It is a generally accepted method for determining the tertiary structure and quaternary structure of purified proteins. SEC is used primarily for the analysis of large molecules such as proteins or polymers. SEC works by trapping these smaller molecules in the pores of a particle. The larger molecules simply pass by the pores as they are too large to enter the pores. Larger molecules therefore flow through the column quicker than smaller molecules, that is, the smaller the molecule, the longer the retention time. Certain compositions are also substantially free of aggregates (greater than about 95% appearing as a single peak by SEC HPLC). Certain embodiments are free of aggregates with greater than about 96%, about 97%, about 98%, or about 99%, appearing as a single peak by SEC HPLC.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The term "solubility" refers to the property of an agent (for example, a fusion protein) described herein to dissolve in a liquid solvent and form a homogeneous solution. Solubility is typically expressed as a concentration, either by mass of solute per unit volume of solvent (g of solute per kg of solvent, g per dL (100 mL), mg/mL, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/mL at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents, for example, fusion proteins.

As used herein, "treatment" of a subject (e.g. a mammal, such as a human) or a cell is any type of intervention used in an attempt to alter the natural course of the individual or cell. Treatment includes, but is not limited to, administration of a composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied mutatis mutandis to every other embodiment unless expressly stated otherwise.

Cytokine Fusion Proteins

Embodiments of the present disclosure relate in part to the unexpected discovery that fusion of at least one cytokine to another, for example, fusion of interleukin-2 (IL-2) to tumor necrosis factor-α (TNF-α), improves the pharmacokinetics and/or biological activity of the fusion protein relative to each cytokine alone. Also related is the discovery that the cytokine fusion proteins can improve the immune response to autologous tumor vaccines, and also improve the anti-tumor activity of immune checkpoint modulatory agents, such as immune checkpoint inhibitors.

Thus, certain embodiments therefore relate to fusion proteins, comprising a first human cytokine fused to the N-terminus of a second human cytokine, wherein the first cytokine differs from the second cytokine. In particular embodiments, the first and second cytokines are selected from human IL-2, TNF-α, IFN-β (IFNB1), IFN-α (for example, IFNA1, IFNA2, IFNA4, IFNA5, IFNA6, IFNA7, IFNA8, IFNA10, IFNA13, IFNA14, IFNA16, IFNA17, IFNA21), IFN-γ, IL-12, GM-CSF, IL-7, IL-23, and IL-27, including variants and/or fragments thereof which have a "cytokine signaling activity" and/or an anti-tumor activity. Exemplary "cytokine signaling activities" are provided below for each cytokine. In some embodiments, the first and second cytokines are separated by a peptide linker.

In some embodiments, the first or second cytokine is human interleukin-2 (IL-2), or a variant and/or fragment thereof having a cytokine signaling activity and/or an anti-tumor activity. IL-2 is produced by T-cells in response to antigenic or mitogenic stimulation, and is required for T-cell proliferation and other activities crucial to regulation of the immune response. It can also stimulate B-cells, monocytes, lymphokine-activated killer cells, natural killer cells, and glioma cells. IL-2 signals through the IL-2 receptor, a complex consisting of three chains, termed alpha, beta, and gamma chains.

In some embodiments, the first or second cytokine is human tumor necrosis factor-α (TNF-α), or a variant and/or fragment thereof having a cytokine signaling activity and/or an anti-tumor activity. TNF-α is a cytokine that binds to TNFRSF1A/TNFR1 and TNFRSF1B/TNFBR. It is mainly secreted by macrophages and can induce cell death of certain tumor cell lines. It exists, for example, in both membrane and soluble forms. The soluble form derives from the membrane form by proteolytic processing. The membrane-bound form is further proteolytically processed by SPPL2A or SPPL2B through regulated intramembrane proteolysis producing TNF intracellular domains (ICD1 and ICD2) released in the cytosol and TNF C-domain 1 and C-domain 2 secreted into the extracellular space. The membrane form, but not the soluble form, is phosphorylated on serine residues. Dephosphorylation of the membrane form occurs by binding to soluble TNFRSF1A/TNFR1.

In some embodiments, the first or second cytokine is a human interferon, or a variant and/or fragment thereof having a cytokine signaling activity and/or an anti-tumor activity. Interferons (IFNs) are a group of cytokine signaling proteins that are released by host cells in response to the presence of tumor cells or pathogens. In some embodiments, the human interferon is a type I interferon such as IFN-α, IFN-β, IFN-ε, IFN-κ, or IFN-ω. Particular examples of IFN-α interferons include IFNA1, IFNA2, IFNA4, IFNA5, IFNA6, IFNA7, IFNA8, IFNA10, IFNA13, IFNA14, IFNA16, IFNA17, IFNA21. In some embodiments, the human interferon is a type II interferon, also known as IFN-γ in humans.

In some embodiments, the first or second cytokine is human interleukin-12 (IL-12), or a variant and/or fragment thereof having a cytokine signaling activity and/or an anti-tumor activity. IL-12 is a cytokine that can act as a growth factor for activated T and NK cells, enhance the lytic activity of NK/lymphokine-activated Killer cells, and stimulate the production of IFN-gamma by resting PBMC. IL-12 is a disulfide-linked heterodimer composed of the IL-12 subunit alpha and IL-12 subunit beta. Certain fusion proteins comprise the subunit alpha, the subunit beta, or both subunits.

In some embodiments, the first or second cytokine is human granulocyte-macrophage colony-stimulating factor (GM-CSF), or a variant and/or fragment thereof having a cytokine signaling activity and/or an anti-tumor activity. GM-CSF is a monomer cytokine that stimulates the growth and differentiation of hematopoietic precursor cells from various lineages, including granulocytes, macrophages, eosinophils, and erythrocytes.

In certain embodiments, the first or second cytokine is human interleukin-7 (IL-7), or a variant and/or fragment thereof having a cytokine signaling activity and/or an anti-tumor activity. IL-7 is hematopoietic growth factor capable of stimulating the proliferation of lymphoid progenitors. For example, it is important for proliferation during certain stages of B-cell maturation.

In particular embodiments, the first or second cytokine is human interleukin-23 (IL-23), or a variant and/or fragment thereof having a cytokine signaling activity and/or an anti-tumor activity. IL-23 is a heterodimeric cytokine which functions in innate and adaptive immunity cytokine, and is composed of the IL-23 subunit alpha and the IL-12 subunit beta. IL-23 binds to a heterodimeric receptor complex composed of IL-12RB1 and IL-23R, activates the Jak-Stat signaling cascade, stimulates memory rather than naive T-cells, and promotes production of proinflammatory cytokines. Certain IL-23 based fusion proteins comprise the IL-23 subunit alpha alone, and certain fusion proteins comprise both the IL-23 subunit alpha and the IL-12 subunit beta.

In some embodiments, the first or second cytokine is human interleukin-27 (IL-27). IL-27 is a heterodimeric cytokine that functions in innate immunity, and is composed of the IL-27 subunit alpha and the IL-27 subunit beta. IL-27 has pro- and anti-inflammatory properties that can regulate T-helper cell development, suppress T-cell proliferation, stimulate cytotoxic T-cell activity, and induce isotype switching in B-cells. It also has diverse effects on innate immune cells. Among its target cells are CD4 T-helper cells which can differentiate in type 1 effector cells (TH1), type 2 effector cells (TH2) and IL17 producing helper T-cells (TH17). It drives rapid clonal expansion of naive but not memory CD4 T-cells. It also synergizes with IL-12 to trigger interferon-gamma/IFN-gamma production of naive CD4 T-cells, and binds to the cytokine receptor WSX-1/TCCR. IL-27 potentiates the early phase of TH1 responses and suppresses TH2 and TH17 differentiation. It induces the differentiation of TH1 cells via two distinct pathways, p38 MAPK/TBX21- and ICAM1/ITGAL/ERK-dependent pathways. It also induces STAT1, STAT3, STAT4 and STAT5 phosphorylation and activates TBX21/T-Bet via STAT1 with resulting IL12RB2 up-regulation, an event crucial to TH1 cell commitment. It suppresses the expression of GATA3, the inhibitor TH1 cells development. In CD8 T-cells, it activates STATs as well as GZMB. IL-27 has also an effect on cytokine production, for example, it suppresses proinflammatory cytokine production such as IL-2, IL-4, IL-5 and IL-6 and activates suppressors of cytokine signaling such as SOCS1 and SOCS3. IL-27 also antagonizes the effects of some cytokines such as IL-6 through direct effects on T-cells. IL-27 also has antitumor activity. Certain IL-27 based fusion proteins comprise the IL-27 subunit alpha alone, the IL-27 subunit beta alone, or both subunits.

The amino acid sequences of the foregoing cytokines are provided in Table C1 below, including certain variants thereof. The skilled artisan will appreciate that, typically, the sequence of the cytokine at the C-terminal portion of the fusion protein will lack the N-terminal methionine residue (from Table C1).

TABLE C1

Exemplary Cytokine Sequences

| Name | Sequence | SEQ ID NO. |
|---|---|---|
| Human IL-2 w/ signal peptide | MYRMQLLSCIALSLALVTNSAPTSSSTKKTQLQLEHLLLDLQMILNGI NNYKNPKLTRMLTFKFYMPKKATELKHLQCLEEELKPLEEVLNLAQSK NFHLRPRDLISNINVIVLELKGSETTFMCEYADETATIVEFLNRWITF CQSIISTLT | 1 |
| Human IL-2 C125S w/ signal peptide | MYRMQLLSCIALSLALVTNSAPTSSSTKKTQLQLEHLLLDLQMILNGI NNYKNPKLTRMLTFKFYMPKKATELKHLQCLEEELKPLEEVLNLAQSK NFHLRPRDLISNINVIVLELKGSETTFMCEYADETATIVEFLNRWITF SQSIISTLT | 2 |
| Human TNF-α Membrane form | MSTESMIRDVELAEEALPKKTGGPQGSRRCLFLSLFSFLIVAGATTLF CLLHFGVIGPQREEFPRDLSLISPLAQAVRSSSRTPSDKPVAHVVANP QAEGQLQWLNRRANALLANGVELRDNQLVVPSEGLYLIYSQVLFKGQG CPSTHVLLTHTISRIAVSYQTKVNLLSAIKSPCQRETPEGAEAKPWYE PIYLGGVFQLEKGDRLSAEINRPDYLDFAESGQVYFGIIAL | 3 |
| Human TNF-α Soluble form | VRSSSRTPSDKPVAHVVANPQAEGQLQWLNRRANALLANGVELRDNQL VVPSEGLYLIYSQVLFKGQGCPSTHVLLTHTISRIAVSYQTKVNLLSA IKSPCQRETPEGAEAKPWYEPIYLGGVFQLEKGDRLSAEINRPDYLDF AESGQVYFGIIAL | 4 |
| Human TNF-α Soluble form R31E | VRSSSRTPSDKPVAHVVANPQAEGQLQWLNERANALLANGVELRDNQL VVPSEGLYLIYSQVLFKGQGCPSTHVLLTHTISRIAVSYQTKVNLLSA IKSPCQRETPEGAEAKPWYEPIYLGGVFQLEKGDRLSAEINRPDYLDF AESGQVYFGIIAL | 5 |
| Human TNF-α Soluble form S86T | VRSSSRTPSDKPVAHVVANPQAEGQLQWLNRRANALLANGVELRDNQL VVPSEGLYLIYSQVLFKGQGCPSTHVLLTHTISRIAVTYQTKVNLLSA IKSPCQRETPEGAEAKPWYEPIYLGGVFQLEKGDRLSAEINRPDYLDF AESGQVYFGIIAL | 6 |
| Human TNF-α Soluble form R31E/S86T | VRSSSRTPSDKPVAHVVANPQAEGQLQWLNERANALLANGVELRDNQL VVPSEGLYLIYSQVLFKGQGCPSTHVLLTHTISRIAVTYQTKVNLLSA IKSPCQRETPEGAEAKPWYEPIYLGGVFQLEKGDRLSAEINRPDYLDF AESGQVYFGIIAL | 7 |
| Human IL-12 Subunit alpha | MCPARSLLLVATLVLLDHLSLARNLPVATPDPGMFPCLHHSQNLLRAV SNMLQKARQTLEFYPCTSEEIDHEDITKDKTSTVEACLPLELTKNESC LNSRETSFITNGSCLASRKTSFMMALCLSSIYEDLKMYQVEFKTMNAK LLMDPKRQIFLDQNMLAVIDELMQALNFNSETVPQKSSLEEPDFYKTK IKLCILLHAFRIRAVTIDRVMSYLNAS | 8 |
| Human IL-12 Subunit beta | MCHQQLVISWFSLVFLASPLVAIWELKKDVYVVELDWYPDAPGEMVVL TCDTPEEDGITWTLDQSSEVLGSGKTLTIQVKEFGDAGQYTCHKGGEV LSHSLLLLHKKEDGIWSTDILKDQKEPKNKTFLRCEAKNYSGRFTCWW LTTISTDLTFSVKSSRGSSDPQGVTCGAATLSAERVRGDNKEYEYSVE CQEDSACPAAEESLPIEVMVDAVHKLKYENYTSSFFIRDIIKPDPPKN LQLKPLKNSRQVEVSWEYPDTWSTPHSYFSLTFCVQVQGKSKREKKDR VFTDKTSATVICRKNASISVRAQDRYYSSSWSEWASVPCS | 9 |
| Human GM-CSF | MWLQSLLLLGTVACSISAPARSPSPSTQPWEHVNAIQEARRLLNLSRD TAAEMNETVEVISEMFDLQEPTCLQTRLELYKQGLRGSLTKLKGPLTM MASHYKQHCPPTPETSCATQIITFESFKENLKDFLLVIPFDCWEPVQE | 10 |
| Human IL-7 | MFHVSFRYIFGLPPLILVLLPVASSDCDIEGKDGKQYESVLMVSIDQL LDSMKEIGSNCLNNEFNFFKRHICDANKEGMFLFRAARKLRQFLKMNS TGDFDLHLLKVSEGTTILLNCTGQVKGRKPAALGEAQPTKSLEENKSL KEQKKLNDLCFLKRLLQEIKTCWNKILMGTKEH | 11 |
| Human IL-23 Subunit alpha | MLGSRAVMLLLLLPWTAQGRAVPGGSSPAWTQCQQLSQKLCTLAWSAH PLVGHMDLREEGDEETTNDVPHIQCGDGCDPQGLRDNSQFCLQRIHQG LIFYEKLLGSDIFTGEPSLLPDSPVGQLHASLLGLSQLLQPEGHHWET QQIPSLSPSQPWQRLLLRFKILRSLQAFVAVAARVFAHGAATLSP | 12 |

TABLE C1-continued

Exemplary Cytokine Sequences

| Name | Sequence | SEQ ID NO. |
|---|---|---|
| Human IL-27 Subunit alpha | MGQTAGDLGWRLSLLLLPLLLVQAGVWGFPRPPGRPQLSLQELRREFT VSLHLARKLLSEVRGQAHRFAESHLPGVNLYLLPLGEQLPDVSLTFQA WRRLSDPERLCFISTTLQPFHALLGGLGTQGRWTNMERMQLWAMRLDL RDLQRHLRFQVLAAGFNLPEEEEEEEEEEEERKGLLPGALGSALQGP AQVSWPQLLSTYRLLHSLELVLSRAVRELLLLSKAGHSVWPLGFPTLS PQP | 13 |
| Human IL-27 Subunit beta | MTPQLLLALVLWASCPPCSGRKGPPAALTLPRVQCRASRYPIAVDCSW TLPPAPNSTSPVSFIATYRLGMAARGHSWPCLQQTPTSTSCTITDVQL FSMAPYVLNVTAVHPWGSSSSFVPFITEHIIKPDPPEGVRLSPLAERQ LQVQWEPPGSWPFPEIFSLKYWIRYKRQGAARFHRVGPIEATSFILRA VRPRARYYVQVAAQDLTDYGELSDWSLPATATMSLGK | 14 |
| Human Interferon beta 1 | MTNKCLLQIALLLCFSTTALSMSYNLLGFLQRSSNFQCQKLLWQLNGR LEYCLKDRMNFDIPEEIKQLQQFQKEDAALTIYEMLQNIFAIFRQDSS STGWNETIVENLLANVYHQINHLKTVLEEKLEKEDFTRGKLMSSLHLK RYYGRILHYLKAKEYSHCAWTIVRVEILRNFYFINRLTGYLRN | 15 |
| Human Interferon alpha 1 | MASPFALLMVLVVLSCKSSCSLGCDLPETHSLDNRRTLMLLAQMSRIS PSSCLMDRHDFGFPQEEFDGNQFQKAPAISVLHELIQQIFNLFTTKDS SAAWDEDLLDKFCTELYQQLNDLEACVMQEERVGETPLMNADSILAVK KYFRRITLYLTEKKYSPCAWEVVRAEIMRSLSLSTNLQERLRRKE | 16 |
| Human Interferon alpha 2 | MALTFALLVALLVLSCKSSCSVGCDLPQTHSLGSRRTLMLLAQMRKIS LFSCLKDRHDFGFPQEEFGNQFQKAETIPVLHEMIQQIFNLFSTKDSS AAWDETLLDKFYTELYQQLNDLEACVIQGVGVTETPLMKEDSILAVRK YFQRITLYLKEKKYSPCAWEVVRAEIMRSFSLSTNLQESLRSKE | 17 |
| Human Interferon gamma | MKYTSYILAFQLCIVLGSLGCYCQDPYVKEAENLKKYFNAGHSDVADN GTLFLGILKNWKEESDRKIMQSQIVSFYFKLFKNFKDDQSIQKSVETI KEDMNVKFFNSNKKKRDDFEKLTNYSVTDLNVQRKAIHELIQVMAELS PAAKTGKRKRSQMLFRGRRASQ | 18 |

Hence, in some embodiments, each cytokine component of the fusion protein comprises, consists, or consists essentially of an amino acid sequence selected from Table C1, or an active variant and/or fragment thereof. Particular examples of active variants and fragments comprise, consist, or consist essentially of an amino acid sequence that is at least 80%, 95%, 90%, 95%, 96%, 97%, 98%, or 99% identical to a sequence selected from Table C1. Additional examples of polypeptide "variants" and "fragments" are described elsewhere herein.

In specific embodiments, the first cytokine is IL-2 and the second cytokine is TNF-α, that is, where IL-2 is fused to the N-terminus of TNF-α, and in some instances is separated by a peptide linker (for example, a -(GGGGS)$_2$ or a -(GGGGS)$_3$-linker (see also Table L1). In some embodiments, the IL-2 comprises, consists, or consists essentially of an amino acid sequence that is at least 90%, 95%, 96%, 97%, 98%, or 99% identical to SEQ ID NO: 1 or 2 (with signal peptide) or residues 21-153 of SEQ ID NO: 1 or 2 (without signal peptide) and has a cytokine signaling activity and/or an anti-tumor activity. In particular embodiments, the IL-2 comprises a C125S or C125A mutation (see, e.g., SEQ ID NO: 2). In some embodiments, the TNF-α comprises, consists, or consists essentially of an amino acid sequence that is at least 90%, 95%, 96%, 97%, 98%, or 99% identical to SEQ ID NO: 3-6 and has a cytokine signaling activity and/or an anti-tumor activity. In particular embodiments, the TNF-α comprises at least one mutation (relative to wild-type) which reduces the specific activity of TNF-α by about or at least about 2, 3, 4, 5, 6, 7, 8, 9, 10, 11, or 12-fold, for example, to a specific activity that is a relative molar equivalent to the specific activity of IL-2. In some embodiments, the TNF-α comprises at least one mutation (relative to wild-type) which increases its preferential binding to TNFR1 relative to TNFR2, for example, by about 1, 2, 3, 4, 5, 6, 7, 8, 9, or 10-fold. In specific embodiments, the TNF-α comprises at least one mutation selected from S86T (see, e.g., SEQ ID NO: 6), R31E (see, e.g., SEQ ID NO: 5), and R32W, including combinations thereof such as S86T/R31E (see, e.g., SEQ ID NO: 7) and S86T/R32W.

In some embodiments, the first cytokine is IFN-β and the second cytokine is TNF-α, that is, where IFN-β is fused to the N-terminus of TNF-α, and in some instances is separated by a peptide linker (for example, a -(GGGGS)$_2$ or a -(GGGGS)$_3$-linker (see also Table L1). In some instances, the IFN-β comprises, consists, or consists essentially of an amino acid sequence that is at least 90%, 95%, 96%, 97%, 98%, or 99% identical to SEQ ID NO: 15 and has a cytokine signaling activity and/or an anti-tumor activity. In some embodiments, the TNF-α comprises, consists, or consists essentially of an amino acid sequence that is at least 90%, 95%, 96%, 97%, 98%, or 99% identical to SEQ ID NO: 3-6 and has a cytokine signaling activity and/or an anti-tumor activity. In particular embodiments, the TNF-α comprises at least one mutation (relative to wild-type) which reduces the specific activity of TNF-α by about or at least about 2, 3, 4, 5, 6, 7, 8, 9, 10, 11, or 12-fold, for example, to a specific activity that is a relative molar equivalent to the specific activity of IFN-3. In some embodiments, the TNF-α comprises at least one mutation (relative to wild-type) which increases its preferential binding to TNFR1 relative to TNFR2, for example, by about 1, 2, 3, 4, 5, 6, 7, 8, 9, or 10-fold. In specific embodiments, the TNF-α comprises at least one mutation selected from S86T (see, e.g., SEQ ID NO: 6), R31E (see, e.g., SEQ ID NO: 5), and R32W, including combinations thereof such as S86T/R31E (see, e.g., SEQ ID NO: 7) and S86T/R32W.

In particular embodiments, the fusion protein comprises the structure:

```
                                            (SEQ ID NO: 19)
IL-2(C125S)-(GGGGS)3-TNF-α (S86T);

(SEQ ID NO: 20)
IL2(C125A)-(GGGGS)2-TNF-α (S86T);

(SEQ ID NO: 21)
IL2(C125A)-(GGGGS)2-TNF-α (R32W);

(SEQ ID NO: 22)
IL2(C125A)-PAPAP-TNF-α (S86T);
```

```
                                            (SEQ ID NO: 23)
IL2(C125A)-PAPAP-TNF-α (R32W);

(SEQ ID NO: 24)
IL2(C125A)-PAEAAAKEAAAKA-TNF-α (S86T);

(SEQ ID NO: 25)
IL2(C125A)-PAEAAAKEAAAKA-TNF-α (R32W);

IL-2(C125S)-(GGGGS)3-TNF-α (R31E, S86T);
or
                                            (SEQ ID NO: 26)
IFN-β-(GGGGS)2-TNF-α
``` including active variants/fragments thereof.

In some embodiments, the fusion protein comprises, consists, or consists essentially of an amino acid sequence selected from Table F1 below.

TABLE F1

| Name | Sequence | SEQ ID NO: |
|---|---|---|
| IL2(C125S)-(GGGGS)3-TNFα(S86T) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLTGGGGSGGGGSGGGGSVRSSSRTPSDKPVAHVVANPQAEGQLQWLNRRANALLANGVELRDNQLVVPSEGLYLIYSQVLFKGQGCPSTHVLLTHTISRIAVTYQTKVNLLSAIKSPCQRETPEGAEAKPWYEPIYLGGVFQLEKGDRLSAEINRPDYLDFAESGQVYFGIIAL | 19 |
| IL2(C125A-(GGGGS)2-TNFα(S86T) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTGGGGSGGGGSVRSSSRTPSDKPVAHVVANPQAEGQLQWLNRRANALLANGVELRDNQLVVPSEGLYLIYSQVLFKGQGCPSTHVLLTHTISRIAVTYQTKVNLLSAIKSPCQRETPEGAEAKPWYEPIYLGGVFQLEKGDRLSAEINRPDYLDFAESGQVYFGIIAL | 20 |
| IL2(C125A)-(GGGGS)2-TNFα(R32W) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTGGGGSGGGGSVRSSSRTPSDKPVAHVVANPQAEGQLQWLNRWANALLANGVELRDNQLVVPSEGLYLIYSQVLFKGQGCPSTHVLLTHTISRIAVSYQTKVNLLSAIKSPCQRETPEGAEAKPWYEPIYLGGVFQLEKGDRLSAEINRPDYLDFAESGQVYFGIIAL | 21 |
| IL2(C125A)-PAPAP-TNFα(S86T) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTPAPAPVRSSSRTPSDKPVAHVVANPQAEGQLQWLNRWANALLANGVELRDNQLVVPSEGLYLIYSQVLFKGQGCPSTHVLLTHTISRIAVTYQTKVNLLSAIKSPCQRETPEGAEAKPWYEPIYLGGVFQLEKGDRLSAEINRPDYLDFAESGQVYFGIIAL | 22 |
| IL2(C125A)-PAPAP-TNFα(R32W) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTPAPAPVRSSSRTPSDKPVAHVVANPQAEGQLQWLNRWANALLANGVELRDNQLVVPSEGLYLIYSQVLFKGQGCPSTHVLLTHTISRIAVSYQTKVNLLSAIKSPCQRETPEGAEAKPWYEPIYLGGVFQLEKGDRLSAEINRPDYLDFAESGQVYFGIIAL | 23 |
| IL2(C125A)-PAEAAAKEAAAKA-TNFα(S86T) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTAEAAAKEAAAKAVRSSSRTPSDKPVAHVVANPQAEGQLQWLNRRANALLANGVELRDNQLVVPSEGLYLIYSQVLFKGQGCPSTHVLLTHTISRIAVSYQTKVNLLSAIKSPCQRETPEGAEAKPWYEPIYLGGVFQLEKGDRLSAEINRPDYLDFAESGQVYFGIIAL | 24 |
| IL2(C125A)-PAEAAAKEAAAKA-TNFα(R32W) | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFAQSIISTLTAEAAAKEAAAKAVRSSSRTPSDKPVAHVVANPQAEGQLQWLNRWANALLANGVELRDNQLVVPSEGLYLIYSQVLFKGQGCPSTHVLLTHTISRIAVSYQTKVNLLSAIKSPCQRETPEGAEAKPWYEPIYLGGVFQLEKGDRLSAEINRPDYLDFAESGQVYFGIIAL | 25 |
| IFNβ-GGGGS2-TNFα | MTNKCLLQIALLLCFSTTALSMSYNLLGFLQRSSNFQCQKLLWQLNGRLEYCLKDRMNFDIPEEIKQLQQFQKEDAALTIYEMLQNIFAIFRQDSSSTGWNETIVENLLANVYHQINHLKTVLEEKLEKEDFTRGKLMSSLHLKRYYGRILHYLKAKEYSHCAWTIVRVEILRNFYFINRLTGYLRNGGGGSGGGGSVRSSSRTPSDK | 26 |

TABLE F1-continued

Exemplary Cytokine Fusion Proteins

| Name | Sequence | SEQ ID NO: |
|---|---|---|
| | PVAHVVANPQAEGQLQWLNRRANALLANGVELRDNQLVVPSEGLYLIYSQVL FKGQGCPSTHLLTHTISRIAVSYQTKVNLLSAIKSPCQRETPEGAEAKPWYE PIYLGGVFQLEKGDRLSAEINRPDYLDFAESGQVYFGIIAL | |

Hence, in some embodiments, the fusion protein comprises, consists, or consists essentially of an amino acid sequence selected from Table F1, or an active variant and/or fragment thereof. Particular examples of active variants and fragments comprise, consist, or consist essentially of an amino acid sequence that is at least 80%, 95%, 90%, 95%, 96%, 97%, 98%, or 99% identical to a sequence selected from Table Ft. Additional examples of polypeptide "variants" and "fragments" are described elsewhere herein.

Linkers. Certain fusion proteins comprise one or more linker peptides. The term "linkage," "linker," "linker moiety," or "L" is used herein to refer to a linker that can be used to separate one polypeptide component of a fusion protein from another polypeptide component, for example, a first cytokine (e.g., JL-2) from a second cytokine (e.g., TNF-α). The peptide linker may be physiologically stable or may include a releasable linker such as a labile linker or an enzymatically degradable linker (e.g., proteolytically cleavable linkers). Peptide linker sequences can be incorporated into a fusion protein using standard techniques in the art.

Certain peptide linker sequences may be chosen based on the following exemplary factors: (1) their ability to adopt a flexible extended conformation; (2) their inability to adopt a secondary structure that could interact with functional epitopes on the first and second polypeptides; (3) their physiological stability; and (4) the lack of hydrophobic or charged residues that might react with the polypeptide functional epitopes, or other features. See, e.g., George and Heringa, J Protein Eng. 15:871-879, 2002. In some embodiments, the peptide linker is a rigid linker. In some embodiments, the peptide linker is a flexible linker. In particular embodiments, flexible linkers can be rationally designed using a computer program capable of modeling the peptides themselves (Desjarlais & Berg, PNAS. 90:2256-2260, 1993; and PNAS. 91:11099-11103, 1994) or by phage display methods.

In some embodiments, the peptide linker sequence is from 1 to about 200 amino acids in length. Exemplary linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., Gene 40:39-46, 1985; Murphy et al., PNAS USA. 83:8258-8262, 1986; U.S. Pat. Nos. 4,935,233 and 4,751,180. Particular peptide linker sequences contain Gly, Ser, and/or Asn residues. Other near neutral amino acids, such as Thr and Ala may also be employed in the peptide linker sequence, if desired.

Certain exemplary peptide linkers are provided in Table L1 below.

TABLE L1

Exemplary Peptide Linkers

| Sequence | SEQ ID NO: |
|---|---|
| $[G]_x$ | |
| $[S]_x$ | |
| $[N]_x$ | |
| $[GS]_x$ | |
| $[GGS]_x$ | |
| $[GSS]_x$ | |
| $[GSGS]_x$ | 27 |
| $[GGSG]_x$ | 28 |
| $[GGGS]_x$ | 29 |
| $[GGGGS]_x$ | 30 |
| $[GN]_x$ | |
| $[GNN]_x$ | |
| $[GNN]_x$ | |
| $[GNGN]_x$ | 31 |
| $[GGNG]_x$ | 32 |
| $[GGGN]_x$ | 33 |
| $[GGGGN]_x$ | 34 |
| $A(EAAAK)_xA$ | 35 |
| AEAAAKA | 35 |
| AEAAAKEAAAKA | 36 |
| $(XP)_x$ | |
| APAPKP | 37 |
| APAPKPEPAPKP | 38 |
| GGGGS | 30 |
| GGGGSGGGGS | 39 |
| DGGGS | 40 |
| TGEKP | 41 |

TABLE L1-continued

Exemplary Peptide Linkers

| Sequence | SEQ ID NO: |
|---|---|
| GGRR | 42 |
| EGKSSGSGSESKVD | 43 |
| KESGSVSSEQLAQFRSLD | 44 |
| GGRRGGGS | 45 |
| LRQRDGERP | 46 |
| LRQKDGGGSERP | 47 |
| LRQKd(GGGS)$_2$ERP | 48 |
| PAPAP | 49 |
| PAEAAAKEAAAKA | 50 |

Where "X" is any amino acid; and
Where "x" is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100

Thus, in certain embodiments, a fusion protein comprises one or more peptide linkers selected from Table P1. In certain embodiments, the foregoing linkers are optional.

Polypeptide Variants. Certain embodiments include "variants" and "fragments" of the reference sequences described herein, whether described by name or by reference to a Table or sequence identifier. Examples include any of the cytokines, fusion proteins, and antibodies described herein. A "variant" sequence refers to a polypeptide or polynucleotide sequence that differs from a reference sequence by one or more substitutions, deletions (e.g., truncations), additions, and/or insertions. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of interactive binding capacity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Tables or the Sequence Listing).

In some embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Tables or the Sequence Listing).

In certain embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In certain instances, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In certain embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (J. Mol. Biol. 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdn CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (Cabios. 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (Nucleic Acids Res. 25: 3389-3402, 1997). When utilizing BLAST and Gapped BLAST programs, the default parameters of the respective programs (e.g., XBLAST and NBLAST) can be used.

In some embodiments, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned segment wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance.

The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In some embodiments, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA*. 89:10915-10919, 1992). GAP uses the algorithm of Needleman and Wunsch (*J Mol Biol*. 48:443-453, 1970) to find the alignment of two complete sequences that maximizes the number of matches and minimizes the number of gaps.

In particular embodiments, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (PNAS USA. 82: 488-492, 1985); Kunkel et al., (Methods in Enzymol. 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, PNAS USA 89: 7811-7815, 1992; Delgrave et al., Protein Engineering. 6: 327-331, 1993).

Polynucleotides, Expression Vectors, and Host Cells. Certain embodiments relate to polynucleotides that encode a fusion protein, as described herein. Thus, certain embodiments include a polynucleotide that encodes a fusion protein comprising any combination of the individual cytokines in Table C1 (including variants and/or fragments thereof), including a fusion protein that comprises any of the linkers in Table L1. Certain embodiments include a polynucleotide that encodes a fusion protein selected from Table F1 (including variants and/or fragments thereof), including a polynucleotide that comprises, consists, or consists essentially of the exemplary coding sequence in Table E1.

Among other uses, these and related embodiments may be utilized to recombinantly produce a fusion polypeptide in a host cell. It will be appreciated by those of ordinary skill in the art that, as a result of the degeneracy of the genetic code, there are many nucleotide sequences that encode a polypeptide described herein. Some of these polynucleotides may bear minimal homology to the nucleotide sequence of any native gene. Nonetheless, polynucleotides that vary due to differences in codon usage are specifically contemplated, for example, polynucleotides that are optimized for human, yeast or bacterial codon selection.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes a fusion polypeptide or a component thereof) or may comprise a variant, or a biological functional equivalent of such a sequence. Polynucleotide variants may contain one or more substitutions, additions, deletions and/or insertions, as described herein, preferably such that the activity of the variant polypeptide is not substantially diminished relative to the unmodified polypeptide.

Additional coding or non-coding sequences may, but need not, be present within a polynucleotide, and a polynucleotide may, but need not, be linked to other molecules and/or support materials. Hence, the polynucleotides, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably.

The polynucleotide sequences may also be of mixed genomic, cDNA, RNA, and that of synthetic origin. For example, a genomic or cDNA sequence encoding a leader peptide may be joined to a genomic or cDNA sequence encoding the polypeptide, after which the DNA or RNA sequence may be modified at a site by inserting synthetic oligonucleotides encoding the desired amino acid sequence for homologous recombination in accordance with well-known procedures or preferably generating the desired sequence by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

One or multiple polynucleotides can encode the fusion proteins described herein. Moreover, the polynucleotide sequence can be manipulated for various reasons. Examples include but are not limited to the incorporation of preferred codons to enhance the expression of the polynucleotide in various organisms (see generally Nakamura et al., Nuc. Acid. Res. 28:292, 2000). In addition, silent mutations can be incorporated in order to introduce, or eliminate restriction sites, decrease the density of CpG dinucleotide motifs (see for example, Kameda et al., Biochem. Biophys. Res. Commun. 349:1269-1277, 2006) or reduce the ability of single stranded sequences to form stem-loop structures: (see, e.g., Zuker M., Nucl. Acid Res. 31:3406-3415, 2003). In addition, mammalian expression can be further optimized by including a Kozak consensus sequence (i.e., (a/g)cc(a/g) ccATGg) (SEQ ID NO: 51) at the start codon. Kozak consensus sequences useful for this purpose are known in the art (Mantyh et al., PNAS 92: 2662-2666, 1995; Mantyh et al., Prot. Exp. & Purif. 6:124, 1995).

Also included are expression vectors that comprise the polynucleotides, and host cells that comprise the polynucleotides and/or expression vectors. Polypeptides and fusion proteins can be produced by expressing a DNA or RNA sequence encoding the polypeptide in a suitable host cell by well-known techniques. The term "host cell" is used to refer to a cell into which has been introduced, or which is capable of having introduced into it, a nucleic acid sequence encoding one or more of the polypeptides described herein, and which further expresses or is capable of expressing a polypeptide of interest, such as a polynucleotide encoding any herein described polypeptide. The term includes the progeny of the parent cell, whether or not the progeny are identical in morphology or in genetic make-up to the original parent, so long as the selected gene is present. Host cells may be chosen for certain characteristics, for instance, the expression of a formylglycine generating enzyme (FGE) to convert a cysteine or serine residue within a sulfatase motif into a formylglycine (FGly) residue, or the expression of aminoacyl tRNA synthetase(s) that can incorporate unnatural amino acids into the polypeptide, including unnatural amino acids with an azide side-chain, alkyne side-chain, or other desired side-chain, to facilitate chemical conjugation or modification.

In some instances, a polynucleotide or expression vector comprises additional non-coding sequences. For example, the "control elements" or "regulatory sequences" present in an expression vector are non-translated regions of the vector, including enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

A variety of expression vector/host systems are known and may be utilized to contain and express polynucleotide sequences. These include, but are not limited to, microorganisms such as bacteria transformed with an expression vector, for example, a recombinant bacteriophage, plasmid, or cosmid DNA expression vector; yeast transformed with yeast expression vectors; insect cell systems infected with viral expression vectors (e.g., baculovirus); plant cell systems transformed with viral expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal, integrating, or other expression vectors. Certain embodiments therefore include an expression vector, comprising a polynucleotide sequence that encodes a polypeptide described herein, for example, a fusion polypeptide. Also included are host cells that comprise the polynucleotides and/or expression vectors.

Certain embodiments may employ *E. coli*-based expression systems (see, e.g., Structural Genomics Consortium et al., Nature Methods. 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series), or modified pET vectors with alternate promoters, including for example the TAC promoter. These and related embodiments may utilize the expression host strain BL21 (DE3), a kDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. In some embodiments other *E. coli* strains may be utilized, including other *E. coli* K-12 strains such as W3110 (F⁻ lambda⁻ IN(rrnD-rrnE)1 rph-1), and UT5600 (F, araC14, leuB6(Am), secA206(aziR), lacY1, proC14, tsx67, Δ(ompTfepC)266, entA403, glnX44(AS), λ⁻, trpE38, rfbC1, rpsL109(strR), xyl A5, mtl-1, thiE1), which can result in reduced levels of post-translational modifications during fermentation. Cell lysis and sample handling may also be improved using reagents sold under the trademarks BENZONASE® nuclease and BUGBUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG.

Particular embodiments employ hexahistidine tags (such as those sold under the trademark HIS•TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., Protein Expr Purif. 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., Nature Biotechnology. 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L. In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544, 1987. Also included are *Pichia pandoris* expression systems (see, e.g., Li et al., Nature Biotechnology. 24, 210-215, 2006; and Hamilton et al., Science, 301:1244, 2003). Certain embodiments include yeast systems that are engineered to selectively glycosylate proteins, including yeast that have humanized N-glycosylation pathways, among others (see, e.g., Hamilton et al., Science. 313:1441-1443, 2006; Wildt et al., Nature Reviews Microbiol. 3:119-28, 2005; and Gerngross et al., Nature-Biotechnology. 22:1409-1414, 2004; U.S. Pat. Nos. 7,629,163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311, 1987). Alternatively, plant promoters such as the small subunit of RUBISCO or heat shock promoters may be used (Coruzzi et al., EMBO J. 3:1671-1680, 1984; Broglie et al., Science. 224:838-843, 1984; and Winter et al., Results Probl. Cell Differ. 17:85-105, 1991). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196, 1992).

An insect system may also be used to express a fusion protein of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., PNAS USA. 91:3224-3227, 1994). Also included are baculovirus expression systems, including those that utilize SF9, SF21, and *T. ni* cells (see, e.g., Murphy and Piwnica-Worms, Curr Protoc Protein Sci. Chapter 5:Unit5.4, 2001). Insect systems can provide post-translation modifications that are similar to mammalian systems.

In mammalian host cells, a number of expression systems are well known in the art and commercially available. Exemplary mammalian vector systems include for example, pCEP4, pREP4, and pREP7 from Invitrogen, the PerC6 system from Crucell, and Lentiviral based systems such as pLP1 from Invitrogen, and others. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, PNAS USA. 81:3655-3659, 1984). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., J. Gen Virol. 36:59, 1977); baby hamster kidney cells (BHK, ATCC CCL 10); mouse sertoli cells (TM4, Mather, Biol. Reprod. 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68, 1982); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA. 77:4216, 1980); and myeloma cell lines such as NSO and Sp2/0. For a review of certain mammalian host cell lines suitable for protein production, see, e.g., Yazaki and Wu, Methods in Molecular Biology, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally occurring amino acids (see generally U.S. Pat. Nos. 7,939,496; 7,816,320; 7,947,473; 7,883,866; 7,838,265; 7,829,310; 7,820,766; 7,820,766; 7,7737,226, 7,736,872; 7,638,299; 7,632,924; and 7,230,068). Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

The skilled artisan will appreciate that the various cytokine fusion proteins described herein can be combined with any one or more of the various autologous tumor cell vaccines and/or immune checkpoint modulatory agents described herein, and used according to any one or more of the methods or compositions described herein.

Autologous Tumor Cell Vaccines

Certain embodiments employ autologous tumor cell vaccines. An autologous tumor cell vaccine comprises tumor cells from a subject being treated (see, for example, Zhang et al., Mol Immunol. 2013 October; 55(3-4):264-74; Fishman et al., J Immunother. 2008 January; 31(1):72-80; Berger et al., J Pharm Sci. 2007; 10(2):144-52; Schirrmacher V., Cancer Immunol Immunother. 2005 June; 54(6):587-98, which are incorporated by reference). In some instances, such vaccines are prepared by isolating tumor cells from the subject and processing or treating these tumor cells into a vaccine formulation in vitro or ex vivo; the vaccine is then administered to the subject from whom the tumor cells were isolated.

General examples include autologous whole cell tumor cell vaccines and autologous tumor cell lysate vaccines. In some instances, the tumor cells are transduced (for example, with a retrovirus that expresses a gene of interest) and then administered to the subject from which they were isolated. In some instances, the tumor cells are irradiated and then administered to the subject from which they were isolated. Also included are dendritic cell (DC)-based autologous tumor cell vaccines, including those in which DCs are isolated from a subject, exposed to tumor cell lysates from the subject, and then administered to the subject (see, for example, Gonzales et al., Hum Vaccin Immunother. 2014; 10(11):3261-9). Certain embodiments thus include autologous tumor lysate-loaded DC vaccines.

In some embodiments, the tumor of the autologous tumor cell vaccine is isolated from a cancer selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer.

In some embodiments, the autologous tumor cell vaccine comprises a cancer antigen selected from one or more of human Her2/neu, Her1/EGF receptor (EGFR), Her3, A33 antigen, B7H3, CD5, CD19, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin $\alpha v \beta 3$, integrin $\alpha 5 \beta 1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin The skilled artisan will appreciate that the various autologous tumor cell vaccines described herein can be combined with any one or more of the various fusion proteins and/or immune checkpoint modulatory agents described herein, and used according to any one or more of the methods or compositions described herein.

Immune Checkpoint Modulatory Agents

Certain embodiments employ one or more immune checkpoint modulatory agent. Particular examples include "antagonists" of one or more inhibitory immune checkpoint molecules, and "agonists" of one or more stimulatory immune checkpoint molecules. Generally, immune checkpoint molecules are components of the immune system that either turn up a signal (co-stimulatory molecules) or turn down a signal, the targeting of which has therapeutic potential in cancer because cancer cells can perturb the natural function of immune checkpoint molecules (see, e.g., Sharma and Allison, Science. 348:56-61, 2015; Topalian et al., Cancer Cell. 27:450-461, 2015; Pardoll, Nature Reviews Cancer. 12:252-264, 2012). In some embodiments, the immune checkpoint modulatory agent (e.g., antagonist, agonist) "binds" or "specifically binds" to the one or more immune checkpoint molecules, as described herein.

In particular embodiments, the immune checkpoint modulatory agent is a polypeptide or peptide. The terms "peptide" and "polypeptide" are used interchangeably herein, however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids, as described herein Antibodies are also included as polypeptides. Thus, in some embodiments, the immune checkpoint modulatory polypeptide agent is an "antibody or an antigen-binding fragment thereof". As used herein, the term "antibody" encompasses not only intact polyclonal or monoclonal antibodies, but also fragments thereof (such as dAb, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. Certain features and characteristics of antibodies (and antigen-binding fragments thereof) are described in greater detail herein.

An antibody or antigen-binding fragment can be of essentially any type. As is well known in the art, an antibody is an immunoglobulin molecule capable of specific binding to a target, such as an immune checkpoint molecule, through at least one epitope recognition site, located in the variable region of the immunoglobulin molecule.

The term "antigen-binding fragment" as used herein refers to a polypeptide fragment that contains at least one CDR of an immunoglobulin heavy and/or light chain that binds to the antigen of interest. In this regard, an antigen-binding fragment of the herein described antibodies may comprise 1, 2, 3, 4, 5, or all 6 CDRs of a VH and $V_L$ sequence from antibodies that bind to a target molecule.

The binding properties of antibodies and antigen-binding fragments thereof can be quantified using methods well known in the art (see Davies et al., Annual Rev. Biochem. 59:439-473, 1990). In some embodiments, an antibody or antigen-binding fragment thereof specifically binds to a target molecule, for example, an immune checkpoint molecule or an epitope or complex thereof, with an equilibrium dissociation constant that is about or ranges from about <10-7 to about 10-8 M. In some embodiments, the equilibrium dissociation constant is about or ranges from about <10-9 M to about <10-10 M. In certain illustrative embodiments, an antibody or antigen-binding fragment thereof has an affinity (Kd) for a target molecule (to which it specifically binds) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

A molecule such as a polypeptide or antibody is said to exhibit "specific binding" or "preferential binding" if it reacts or associates more frequently, more rapidly, with greater duration and/or with greater affinity with a particular cell, substance, or particular epitope than it does with alternative cells or substances, or epitopes. An antibody "specifically binds" or "preferentially binds" to a target molecule or epitope if it binds with greater affinity, avidity, more readily, and/or with greater duration than it binds to other substances or epitopes, for example, by a statistically significant amount. Typically one member of the pair of molecules that exhibit specific binding has an area on its surface, or a cavity, which specifically binds to and is therefore complementary to a particular spatial and/or polar organization of the other member of the pair of molecules. Thus, the members of the pair have the property of binding specifically to each other. For instance, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. The term is also applicable where, for example, an antibody is specific for a particular epitope which is carried by a number of antigens, in which case the specific binding member carrying the antigen-binding fragment or domain will be able to bind to the various antigens carrying the epitope; for example, it may be cross reactive to a number of different forms of a target antigen from multiple species that share a common epitope Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant (Kd) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and the actual rates of association and dissociation. The ratio of Koff/Kon enables cancellation of all parameters not related to affinity, and is thus equal to the dissociation constant Kd. As used herein, the term "affinity" includes the equilibrium constant for the reversible binding of two agents and is expressed as Kd.

Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S. Pat. No. 7,244,592; Chao et al., Nature Protocols. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

Also include are "monoclonal" antibodies, which refer to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent VH::VL heterodimer including an antigen-binding site which retains much of the antigen recognition and binding capabilities of the native antibody molecule. See Inbar et al., PNAS USA. 69:2659-2662, 1972;

Hochman et al., Biochem. 15:2706-2710, 1976; and Ehrlich et al., Biochem. 19:4091-4096, 1980.

In certain embodiments, single chain Fv (scFV) antibodies are contemplated. For example, Kappa bodies (Ill et al., Prot. Eng. 10:949-57, 1997); minibodies (Martin et al., EMBO J 13:5305-9, 1994); diabodies (Holliger et al., PNAS 90: 6444-8, 1993); or Janusins (Traunecker et al., EMBO J 10: 3655-59, 1991; and Traunecker et al., Int. J. Cancer Suppl. 7:51-52, 1992), may be prepared using standard molecular biology techniques following the teachings of the present application with regard to selecting antibodies having the desired specificity.

A single chain Fv (scFv) polypeptide is a covalently linked VH::VL heterodimer which is expressed from a gene fusion including VH- and VL-encoding genes linked by a peptide-encoding linker. Huston et al. (PNAS USA. 85(16): 5879-5883, 1988). A number of methods have been described to discern chemical structures for converting the naturally aggregated—but chemically separated-light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., PNAS USA 86:4220-4224, 1989; Queen et al., PNAS USA. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., Cancer Res. 53:851-856, 1993; Riechmann et al., Nature 332:323-327, 1988; Verhoeyen et al., Science 239:1534-1536, 1988; Kettleborough et al., Protein Engineering. 4:773-3783, 1991; Maeda et al., Human Antibodies Hybridoma 2:124-134, 1991; Gorman et al., PNAS USA. 88:4181-4185, 1991; Tempest et al., Bio/Technology 9:266-271, 1991; Co et al., PNAS USA. 88:2869-2873, 1991; Carter et al., PNAS USA. 89:4285-4289, 1992; and Co et al., J Immunol. 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In some embodiments, the agent is or comprises a "ligand," for example, a natural ligand, of the immune checkpoint molecule. A "ligand" refers generally to a substance or molecule that forms a complex with a target molecule (e.g., biomolecule) to serve a biological purpose, and includes a "protein ligand," which generally produces a signal by binding to a site on a target molecule or target protein. Thus, certain agents are protein ligands that, in nature, bind to an immune checkpoint molecule and produce a signal. Also included are "modified ligands," for example, protein ligands that are fused to a pharmacokinetic modifier, for example, an Fc region derived from an immunoglobulin.

The binding properties of ligands can be quantified using methods well known in the art (see Davies et al., Annual Rev. Biochem. 59:439-473, 1990). In some embodiments, a ligand specifically binds to a target molecule, for example, an immune checkpoint molecule or an epitope thereof, with an equilibrium dissociation constant that is about or ranges from about <$10^{-7}$ to about $10^{-8}$ M. In some embodiments, the equilibrium dissociation constant is about or ranges from about <$10^{-9}$ M to about <$10^{-10}$ M. In certain illustrative embodiments, the ligand has an affinity (Kd) for a target described herein (to which it specifically binds) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the agent is a "small molecule," which refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of about or less than about 1000-2000 Daltons, typically between about 300 and 700 Daltons, and including about or less than about 50, 100, 150, 200, 250, 300, 350, 400, 450, 500, 550, 500, 650, 600, 750, 700, 850, 800, 950, 1000 or 2000 Daltons.

Certain small molecules can have the "specific binding" characteristics described for herein polypeptides such as antibodies. For instance, in some embodiments a small molecule specifically binds to a target, for example, an immune checkpoint molecule, with a binding affinity (Kd) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the immune checkpoint modulatory agent is an antagonist or inhibitor of one or more inhibitory immune checkpoint molecules. Exemplary inhibitory immune checkpoint molecules include Programmed Death-Ligand 1 (PD-L1), Programmed Death-Ligand 2 (PD-L2), Programmed Death 1 (PD-1), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, and T-cell immunoreceptor with Ig and ITIM domains (TIGIT).

In certain embodiments, the agent is a PD-1 (receptor) antagonist or inhibitor, the targeting of which has been shown to restore immune function in the tumor environment (see, e.g., Phillips et al., Int Immunol. 27:39-46, 2015). PD-1 is a cell surface receptor that belongs to the immunoglobulin superfamily and is expressed on T cells and pro-B cells. PD-1 interacts with two ligands, PD-L1 and PD-L2. PD-1 functions as an inhibitory immune checkpoint molecule, for example, by reducing or preventing the activation of T-cells, which in turn reduces autoimmunity and promotes self-tolerance. The inhibitory effect of PD-1 is accomplished at least in part through a dual mechanism of promoting apoptosis in antigen specific T-cells in lymph nodes while also reducing apoptosis in regulatory T cells (suppressor T cells). Some examples of PD-1 antagonists or inhibitors include an antibody or antigen-binding fragment or small molecule that specifically binds to PD-1 and reduces one or more of its immune-suppressive activities, for example, its downstream signaling or its interaction with PD-L1. Specific examples of PD-1 antagonists or inhibitors include the antibodies nivolumab, pembrolizumab, PDR001, MK-3475, AMP-224, AMP-514, and pidilizumab, and antigen-binding fragments thereof (see, e.g., U.S. Pat. Nos. 8,008,449; 8,993,731; 9,073,994; 9,084,776; 9,102,727; 9,102,728; 9,181,342; 9,217,034; 9,387,247; 9,492,539; 9,492,540; and U.S. Application Nos. 2012/0039906; 2015/0203579).

In some embodiments, the agent is a PD-L1 antagonist or inhibitor. As noted above, PD-L1 is one of the natural ligands for the PD-1 receptor. General examples of PD-L1 antagonists or inhibitors include an antibody or antigen-binding fragment or small molecule that specifically binds to PD-L1 and reduces one or more of its immune-suppressive activities, for example, its binding to the PD-1 receptor. Specific examples of PD-L1 antagonists include the antibodies atezolizumab (MPDL3280A), avelumab (MSB0010718C), and durvalumab (MEDI4736), and antigen-binding fragments thereof (see, e.g., U.S. Pat. Nos. 9,102,725; 9,393,301; 9,402,899; 9,439,962).

In some embodiments, the agent is a PD-L2 antagonist or inhibitor. As noted above, PD-L2 is one of the natural ligands for the PD-1 receptor. General examples of PD-L2 antagonists or inhibitors include an antibody or antigen-binding fragment or small molecule that specifically binds to PD-L2 and reduces one or more of its immune-suppressive activities, for example, its binding to the PD-1 receptor.

In some embodiments, the agent is a CTLA-4 antagonist or inhibitor. CTLA4 or CTLA-4 (cytotoxic T-lymphocyte-associated protein 4), also known as CD152 (cluster of differentiation 152), is a protein receptor that functions as an inhibitory immune checkpoint molecule, for example, by transmitting inhibitory signals to T-cells when it is bound to CD80 or CD86 on the surface of antigen-presenting cells. General examples CTLA-4 antagonists or inhibitors include an antibody or antigen-binding fragment or small molecule that specifically binds to CTLA-4. Particular examples include the antibodies ipilimumab and tremelimumab, and antigen-binding fragments thereof. At least some of the activity of ipilimumab is believed to be mediated by antibody-dependent cell-mediated cytotoxicity (ADCC) killing of suppressor Tregs that express CTLA-4.

In some embodiments, the agent is an IDO antagonist or inhibitor, or a TDO antagonist or inhibitor. IDO and TDO are tryptophan catabolic enzymes with immune-inhibitory properties. For example, IDO is known to suppress T-cells and NK cells, generate and activate Tregs and myeloid-derived suppressor cells, and promote tumor angiogenesis. General examples of IDO and TDO antagonists or inhibitors include an antibody or antigen-binding fragment or small molecule that specifically binds to IDO or TDO (see, e.g., Platten et al., Front Immunol. 5: 673, 2014) and reduces or inhibits one or more immune-suppressive activities. Specific examples of IDO antagonists or inhibitors include indoximod (NLG-8189), 1-methyl-tryptophan (1MT), β-Carboline (norharmane; 9H-pyrido[3,4-b]indole), rosmarinic acid, and epacadostat (see, e.g., Sheridan, Nature Biotechnology. 33:321-322, 2015). Specific examples of TDO antagonists or inhibitors include 680C91 and LM10 (see, e.g., Pilotte et al., PNAS USA. 109:2497-2502, 2012).

In some embodiments, the agent is a TIM-3 antagonist or inhibitor. T-cell Immunoglobulin domain and Mucin domain 3 (TIM-3) is expressed on activated human CD4+ T-cells and regulates Th1 and Th17 cytokines. TIM-3 also acts as a negative regulator of Th1/Tc1 function by triggering cell death upon interaction with its ligand, galectin-9. TIM-3 contributes to the suppressive tumor microenvironment and its overexpression is associated with poor prognosis in a variety of cancers (see, e.g., Li et al., Acta Oncol. 54:1706-13, 2015). General examples of TIM-3 antagonists or inhibitors include an antibody or antigen-binding fragment or small molecule that specifically binds to TIM-3 and reduces or inhibits one or more of its immune-suppressive activities.

In some embodiments, the agent is a LAG-3 antagonist or inhibitor. Lymphocyte Activation Gene-3 (LAG-3) is expressed on activated T-cells, natural killer cells, B-cells and plasmacytoid dendritic cells. It negatively regulates cellular proliferation, activation, and homeostasis of T-cells, in a similar fashion to CTLA-4 and PD-1 (see, e.g., Workman and Vignali. European Journal of Immun. 33: 970-9, 2003; and Workman et al., Journal of Immun. 172: 5450-5, 2004), and has been reported to play a role in Treg suppressive function (see, e.g., Huang et al., Immunity. 21: 503-13, 2004). LAG3 also maintains CD8+ T-cells in a tolerogenic state and combines with PD-1 to maintain CD8 T-cell exhaustion. General examples of LAG-3 antagonists or inhibitors include an antibody or antigen-binding fragment or small molecule that specifically binds to LAG-3 and inhibits one or more of its immune-suppressive activities. Specific examples include the antibody BMS-986016, and antigen-binding fragments thereof.

In some embodiments, the agent is a VISTA antagonist or inhibitor. V-domain Ig suppressor of T cell activation (VISTA) is primarily expressed on hematopoietic cells and is an inhibitory immune checkpoint regulator that suppresses T-cell activation, induces Foxp3 expression, and is highly expressed within the tumor microenvironment where it suppresses anti-tumor T cell responses (see, e.g., Lines et al., Cancer Res. 74:1924-32, 2014). General examples of VISTA antagonists or inhibitors include an antibody or antigen-binding fragment or small molecule that specifically binds to VISTA and reduces one or more of its immune-suppressive activities.

In some embodiments, the agent is a BTLA antagonist or inhibitor. B- and T-lymphocyte attenuator (BTLA; CD272) expression is induced during activation of T-cells, and it inhibits T-cells via interaction with tumor necrosis family receptors (TNF-R) and B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses, for example, by inhibiting the function of human CD8+ cancer-specific T-cells (see, e.g., Derré et al., J Clin Invest 120:157-67, 2009). General examples of BTLA antagonists or inhibitors include an antibody or antigen-binding fragment or small molecule that specifically binds to BTLA-4 and reduce one or more of its immune-suppressive activities.

In some embodiments, the agent is an HVEM antagonist or inhibitor, for example, an antagonist or inhibitor that specifically binds to HVEM and interferes with its interaction with BTLA or CD160. General examples of HVEM antagonists or inhibitors include an antibody or antigen-binding fragment or small molecule that specifically binds to HVEM, optionally reduces the HVEM/BTLA and/or HVEM/CD160 interaction, and thereby reduces one or more of the immune-suppressive activities of HVEM.

In some embodiments, the agent is a CD160 antagonist or inhibitor, for example, an antagonist or inhibitor that specifically binds to CD160 and interferes with its interaction with HVEM. General examples of CD160 antagonists or inhibitors include an antibody or antigen-binding fragment or small molecule that specifically binds to CD160, optionally reduces the CD160/HVEM interaction, and thereby reduces or inhibits one or more of its immune-suppressive activities.

In some embodiments, the agent is a TIGIT antagonist or inhibitor. T cell Ig and ITIM domain (TIGIT) is a coinhibitory receptor that is found on the surface of a variety of lymphoid cells, and suppresses antitumor immunity, for example, via Tregs (Kurtulus et al., J Clin Invest. 125:4053-4062, 2015). General examples of TIGIT antagonists or inhibitors include an antibody or antigen-binding fragment or small molecule that specifically binds to TIGIT and reduce one or more of its immune-suppressive activities (see, e.g., Johnston et al., Cancer Cell. 26:923-37, 2014).

In certain embodiments, the immune checkpoint modulatory agent is an agonist of one or more stimulatory immune checkpoint molecules. Exemplary stimulatory immune checkpoint molecules include OX40, CD40, Glucocorticoid-Induced TNFR Family Related Gene (GITR), CD137 (4-1BB), CD27, CD28, CD226, and Herpes Virus Entry Mediator (HVEM).

In some embodiments, the agent is an OX40 agonist. OX40 (CD134) promotes the expansion of effector and memory T cells, and suppresses the differentiation and activity of T-regulatory cells (see, e.g., Croft et al., Immunol Rev. 229:173-91, 2009). Its ligand is OX40L (CD252). Since OX40 signaling influences both T-cell activation and survival, it plays a key role in the initiation of an anti-tumor immune response in the lymph node and in the maintenance of the anti-tumor immune response in the tumor microenvironment. General examples of OX40 agonists include an antibody or antigen-binding fragment or small molecule or ligand that specifically binds to OX40 and increases one or more of its immunostimulatory activities. Specific examples include OX86, OX-40L, Fc-OX40L, GSK3174998, MEDI0562 (a humanized OX40 agonist), MEDI6469 (murine OX4 agonist), and MEDI6383 (an OX40 agonist), and antigen-binding fragments thereof.

In some embodiments, the agent is a CD40 agonist. CD40 is expressed on antigen-presenting cells (APC) and some malignancies. Its ligand is CD40L (CD154). On APC, ligation results in upregulation of costimulatory molecules, potentially bypassing the need for T-cell assistance in an antitumor immune response. CD40 agonist therapy plays an important role in APC maturation and their migration from the tumor to the lymph nodes, resulting in elevated antigen presentation and T cell activation. Anti-CD40 agonist antibodies produce substantial responses and durable anticancer immunity in animal models, an effect mediated at least in part by cytotoxic T-cells (see, e.g., Johnson et al. Clin Cancer Res. 21: 1321-1328, 2015; and Vonderheide and Glennie, Clin Cancer Res. 19:1035-43, 2013). General examples of CD40 agonists include an antibody or antigen-binding fragment or small molecule or ligand that specifically binds to CD40 and increases one or more of its immunostimulatory activities. Specific examples include CP-870,893, dacetuzumab, Chi Lob 7/4, ADC-1013, CD40L, rhCD40L, and antigen-binding fragments thereof.

In some embodiments, the agent is a GITR agonist. Glucocorticoid-Induced TNFR family Related gene (GITR) increases T cell expansion, inhibits the suppressive activity of Tregs, and extends the survival of T-effector cells. GITR agonists have been shown to promote an anti-tumor response through loss of Treg lineage stability (see, e.g., Schaer et al., Cancer Immunol Res. 1:320-31, 2013). These diverse mechanisms show that GITR plays an important role in initiating the immune response in the lymph nodes and in maintaining the immune response in the tumor tissue. Its ligand is GITRL. General examples of GITR agonists include an antibody or antigen-binding fragment or small molecule or ligand that specifically binds to GITR and increases one or more of its immunostimulatory activities. Specific examples include GITRL, INCAGN01876, DTA-1, MEDI1873, and antigen-binding fragments thereof.

In some embodiments, the agent is a CD137 agonist. CD137 (4-1BB) is a member of the tumor necrosis factor (TNF) receptor family, and crosslinking of CD137 enhances T-cell proliferation, IL-2 secretion, survival, and cytolytic activity. CD137-mediated signaling also protects T-cells such as CD8+ T-cells from activation-induced cell death. General examples of CD137 agonists include an antibody or antigen-binding fragment or small molecule or ligand that specifically binds to CD137 and increases one or more of its immunostimulatory activities. Specific examples include the CD137 (or 4-1BB) ligand (see, e.g., Shao and Schwarz, J Leukoc Biol. 89:21-9, 2011) and the antibody utomilumab, including antigen-binding fragments thereof.

In some embodiments, the agent is a CD27 agonist. Stimulation of CD27 increases antigen-specific expansion of naïve T cells and contributes to T-cell memory and long-term maintenance of T-cell immunity. Its ligand is CD70. The targeting of human CD27 with an agonist antibody stimulates T-cell activation and antitumor immunity (see, e.g., Thomas et al., Oncoimmunology. 2014; 3:e27255. doi:10.4161/onci.27255; and He et al., J Immunol. 191: 4174-83, 2013). General examples of CD27 agonists include an antibody or antigen-binding fragment or small molecule or ligand that specifically binds to CD27 and increases one or more of its immunostimulatory activities. Specific examples include CD70 and the antibodies varlilumab and CDX-1127 (1F5), including antigen-binding fragments thereof.

In some embodiments, the agent is a CD28 agonist. CD28 is constitutively expressed CD4+ T cells some CD8+ T cells. Its ligands include CD80 and CD86, and its stimulation increases T-cell expansion. General examples of CD28 agonists include an antibody or antigen-binding fragment or small molecule or ligand that specifically binds to CD28 and increases one or more of its immunostimulatory activities. Specific examples include CD80, CD86, the antibody TAB08, and antigen-binding fragments thereof.

In some embodiments, the agent is CD226 agonist. CD226 is a stimulating receptor that shares ligands with TIGIT, and opposite to TIGIT, engagement of CD226 enhances T-cell activation (see, e.g., Kurtulus et al., J Clin Invest. 125:4053-4062, 2015; Bottino et al., J Exp Med. 1984:557-567, 2003; and Tahara-Hanaoka et al., Int Immunol. 16:533-538, 2004). General examples of CD226 agonists include an antibody or antigen-binding fragment or small molecule or ligand (e.g., CD112, CD155) that specifically binds to CD226 and increases one or more of its immunostimulatory activities.

In some embodiments, the agent is an HVEM agonist. Herpesvirus entry mediator (HVEM), also known as tumor necrosis factor receptor superfamily member 14 (TNFRSF14), is a human cell surface receptor of the TNF-receptor superfamily. HVEM is found on a variety of cells including T-cells, APCs, and other immune cells. Unlike other receptors, HVEM is expressed at high levels on resting T-cells and down-regulated upon activation. It has been shown that HVEM signaling plays a crucial role in the early phases of T-cell activation and during the expansion of tumor-specific lymphocyte populations in the lymph nodes. General examples of HVEM agonists include an antibody or antigen-binding fragment or small molecule or ligand that specifically binds to HVEM and increases one or more of its immunostimulatory activities.

The skilled artisan will appreciate that the various immune checkpoint modulatory agents described herein can be combined with any one or more of the various fusion proteins and/or autologous tumor cell vaccines described herein, and used according to any one or more of the methods or compositions described herein.

Methods of Use and Compositions Formulations

Also included are methods of using the cytokine fusion proteins described herein for treating a subject in need thereof, and compositions comprising the fusion proteins. For example, certain embodiments include methods of treating, ameliorating the symptoms of, or inhibiting the progression of, a cancer in a subject in need thereof, comprising administering to the subject a cytokine fusion protein described herein, or a composition comprising the fusion protein. Certain embodiments include reducing or preventing the re-emergence of a cancer in a subject in need thereof, for example, a metastatic cancer, wherein administration of the therapeutic composition enables generation of an immune memory to the cancer.

Also include are combination therapies for treating cancers, including methods of treating ameliorating the symptoms of, or inhibiting the progression of, a cancer in a subject in need thereof, comprising administering to the subject at least one cytokine fusion protein in combination with at least one autologous tumor cell vaccine (obtained from the subject in need thereof). Some combination therapies include methods of treating ameliorating the symptoms of, or inhibiting the progression of, a cancer in a subject in need thereof, comprising administering to the subject at least one cytokine fusion protein in combination with at least one checkpoint modulatory agent. Specific combination therapies include methods of treating ameliorating the symptoms of, or inhibiting the progression of, a cancer in a subject in need thereof, comprising administering to the subject at least one cytokine fusion protein in combination with at least one autologous tumor cell vaccine (obtained from the subject in need thereof) and at least one checkpoint modulatory agent. Exemplary cytokine fusion proteins, autologous tumor cell vaccines, immune checkpoint modulatory agents, and therapeutic or vaccine compositions comprising the same, are described elsewhere herein.

In some instances, a cytokine fusion protein and an autologous tumor cell vaccine are administered as part of the same therapeutic or vaccine composition. In some instances, a cytokine fusion protein and a immune checkpoint modulatory agent are administered as part of the same therapeutic or vaccine composition. In particular instances, In some instances, a cytokine fusion protein, an autologous tumor cell vaccine, and an immune checkpoint modulatory agent are administered as part of the same therapeutic or vaccine composition. In certain instances, one or more of the combination therapy agents (i.e., cytokine fusion protein, autologous tumor vaccine, and/or immune checkpoint modulatory agent) are administered separately, as separate therapeutic or vaccine compositions.

In some embodiments, the methods and compositions described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, the methods or compositions described herein increase median survival time of a patient by 1 year, 2 years, 3 years, or longer. In some embodiments, the methods and compositions described herein increase progression-free survival by 2 weeks, 3 weeks, 4 weeks, 5 weeks, 6 weeks, 7 weeks, 8 weeks, 9 weeks, 10 weeks or longer. In certain embodiments, the methods and compositions described herein increase progression-free survival by 1 year, 2 years, 3 years, or longer.

In certain embodiments, a composition administered is sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, a composition administered is sufficient to result in stable disease. In certain embodiments, a composition administered is sufficient to result in stabilization or clinically relevant reduction in symptoms of a particular disease indication known to the skilled clinician.

The methods and compositions for treating cancers can be combined with other therapeutic modalities. For example, one or more agents or compositions described herein can be administered to a subject before, during, or after other therapeutic interventions, including symptomatic care, chemotherapy, radiotherapy, surgery, transplantation, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

The methods and compositions described herein can be used in the treatment of any variety of cancers. In some embodiments, the cancer is a primary cancer, i.e., a cancer growing at the anatomical site where tumor progression began and yielded a cancerous mass. In some embodiments, the cancer is a secondary or metastatic cancer, i.e., a cancer which has spread from the primary site or tissue of origin into one or more different sites or tissues. In some embodiments, the subject or patient has a cancer selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma or HCC), sarcoma, B-cell malignancy, breast cancer (for example, estrogen receptor positive (ER+), estrogen receptor negative (ER−), Her2 positive (Her2+), Her2 negative (Her2−), or a combination thereof, e.g., ER+/Her2+, ER+/Her2−, ER−/Her2+, or ER−/Her2−; or "triple negative" breast cancer which is estrogen receptor-negative, progesterone receptor-negative, and HER2-negative), ovarian cancer, colorectal cancer, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, stomach cancer, virus-induced tumors such as, for example, papilloma virus-induced carcinomas (e.g., cervical carcinoma, cervical cancer), adenocarcinomas, herpes virus-induced tumors (e.g. Burkitt's lymphoma, EBV-induced B-cell lymphoma), hepatitis B-induced tumors (hepatocellular carcinomas), HTLV-1-induced and HTLV-2-induced lymphomas, acoustic neuroma, lung cancers (e.g., lung carcinoma, bronchial carcinoma), small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal cancer (e.g., oesophageal carcinoma), wart involvement, tumors of the small intestine, craniopharyngeomas, ovarian carcinoma, genital tumors, ovarian cancer (e.g., ovarian carcinoma), pancreatic cancer (e.g., pancreatic carcinoma), endometrial carcinoma, liver metastases, penile cancer, tongue cancer, gall bladder cancer, leukaemia, plasmocytoma, and lid tumor.

In some embodiments, as noted above, the cancer or tumor is a metastatic cancer. Further to the above cancers, exemplary metastatic cancers include, without limitation, bladder cancers which have metastasized to the bone, liver, and/or lungs; breast cancers which have metastasized to the bone, brain, liver, and/or lungs; colorectal cancers which have metastasized to the liver, lungs, and/or peritoneum; kidney cancers which have metastasized to the adrenal glands, bone, brain, liver, and/or lungs; lung cancers which have metastasized to the adrenal glands, bone, brain, liver, and/or other lung sites; melanomas which have metastasized to the bone, brain, liver, lung, and/or skin/muscle; ovarian cancers which have metastasized to the liver, lung, and/or peritoneum; pancreatic cancers which have metastasized to the liver, lung, and/or peritoneum; prostate cancers which have metastasized to the adrenal glands, bone, liver, and/or lungs; stomach cancers which have metastasized to the liver, lung, and/or peritoneum; thyroid cancers which have metastasized to the bone, liver, and/or lungs; and uterine cancers which have metastasized to the bone, liver, lung, peritoneum, and/or vagina; among others.

In some embodiments, for example, where the cancer immunotherapy agent is a PD-1 or PD-L1 antagonist or inhibitor, the subject has one or more biomarkers (e.g., increased PD-1 or PD-L1 levels in cells such as cancer cells or cancer-specific CTLs) that make the suitable for PD-1 or PD-L1 inhibitor therapy. For instance, in some embodiments, the subject has increased fractions of programmed cell death 1 high/cytotoxic T lymphocyte-associated protein 4 high (e.g., PD-1$^{hi}$CTLA-4$^{hi}$) cells within a tumor-infiltrating CD8+ T cell subset (see, e.g., Daud et al., J Clin Invest. 126:3447-3452, 2016). As another example, in some embodiments, the subject has increased levels of Bim (B cell lymphoma 2-interacting (Bcl2-interacting) mediator) in circulating tumor-reactive (e.g., PD-1$^+$CD11a$^{hi}$CD8$^+$) T cells, and optionally has metastatic melanoma (see, e.g., Dronca et al., JCI Insight. May 5; 1(6): e86014, 2016).

Certain specific combinations include a cytokine fusion protein and a PD-L1 antagonist or inhibitor, for example, atezolizumab (MPDL3280A), avelumab (MSB0010718C), and durvalumab (MED14736), for treating a cancer selected from one or more of colorectal cancer, melanoma, breast cancer, non-small-cell lung carcinoma, bladder cancer, and renal cell carcinoma.

Some specific combinations include a cytokine fusion protein and a PD-1 antagonist, for example, nivolumab, for treating a cancer selected from one or more of Hodgkin's lymphoma, melanoma, non-small cell lung cancer, hepatocellular carcinoma, renal cell carcinoma, and ovarian cancer.

Particular specific combinations include a cytokine fusion protein and a PD-1 antagonist, for example, pembrolizumab, for treating a cancer selected from one or more of melanoma, non-small cell lung cancer, small cell lung cancer, head and neck cancer, and urothelial cancer.

Certain specific combinations include a cytokine fusion protein and a CTLA-4 antagonist, for example, ipilimumab and tremelimumab, for treating a cancer selected from one or more of melanoma, prostate cancer, lung cancer, and bladder cancer.

Some specific combinations include a cytokine fusion protein and an IDO antagonist, for example, indoximod (NLG-8189), 1-methyl-tryptophan (1MT), β-Carboline (norharmane; 9H-pyrido[3,4-b]indole), rosmarinic acid, or epacadostat, for treating a cancer selected from one or more of metastatic breast cancer and brain cancer optionally Glioblastoma Multiforme, glioma, gliosarcoma or malignant brain tumor.

Methods for identifying subjects with one or more of the diseases or conditions described herein are known in the art.

For in vivo use, for instance, for the treatment of human disease or testing, the fusion proteins described herein are generally incorporated into one or more compositions prior to administration, including pharmaceutical, therapeutic, and/or vaccine compositions. In some instances, a composition comprises at least one cytokine fusion protein described herein in combination with a physiologically acceptable carrier or excipient. In some instances, a composition comprising at least one cytokine fusion protein further comprises an autologous tumor cell vaccine. In some embodiments, a composition comprising at least one cytokine fusion protein further comprises at least one immune checkpoint modulatory agent. In specific embodiments, a composition comprising at least one cytokine fusion protein further comprises an autologous tumor cell vaccine and an immune checkpoint modulatory agent.

Some compositions comprise (and certain methods utilize) only one cytokine fusion protein. Certain compositions comprise (and certain methods utilize) a mixture of at least two, three, four, or five different cytokine fusion proteins.

In particular embodiments, the composition comprising the agents such as cytokine fusion proteins, antibodies, and/or other polypeptide agents is substantially pure on a protein basis or a weight-weight basis, for example, wherein the composition has a purity of at least about 80%, 85%, 90%, 95%, 98%, or 99% on a protein basis or a weight-weight basis.

In some embodiments, the cytokine fusion proteins or other polypeptide agents provided herein do not form aggregates, have a desired solubility, and/or have an immunogenicity profile that is suitable for use in humans, as described herein and known in the art. Thus, in some embodiments, the therapeutic composition comprising a polypeptide agent (for example, cytokine fusion protein and optionally an antibody) is substantially aggregate-free. For example, certain compositions comprise less than about 10% (on a protein basis) high molecular weight aggregated proteins, or less than about 5% high molecular weight aggregated proteins, or less than about 4% high molecular weight aggregated proteins, or less than about 3% high molecular weight aggregated proteins, or less than about 2% high molecular weight aggregated proteins, or less than about 1% high molecular weight aggregated proteins. Some compositions comprise a polypeptide agent (e.g., cytokine fusion protein and optionally an antibody) that is at least about 50%, about 60%, about 70%, about 80%, about 90% or about 95% monodisperse with respect to its apparent molecular mass.

In some embodiments, polypeptide agents are concentrated to about or at least about 0.1 mg/ml, 0.2 mg/ml, 0.3 mg/ml, 0.4 mg/ml, 0.5 mg/ml, 0.6, 0.7, 0.8, 0.9, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11, 12, 13, 14 or 15 mg/ml and are formulated for biotherapeutic uses.

To prepare a composition (e.g., a pharmaceutical, therapeutic, and/or vaccine composition), an effective or desired amount of one or more agents is mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of agents described herein, in pure form or in an appropriate composition, can be carried out via any of the accepted modes of administration of agents for serving similar utilities. The compositions can be prepared by combining an agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Carriers can include, for example, pharmaceutically- or physiologically-acceptable carriers, excipients, or stabilizers that are non-toxic to the cell or mammal being exposed thereto at the dosages and concentrations employed. Often the physiologically-acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art. Particular embodiments thus include compositions that comprise an extended time release formulation. Examples include compositions that comprise any one or more of poly(lactic-co-glycolic acid) (PLGA), polyethylene glycol (PEG), poly (lactic acid) (PLA), poly(glycolic acid) (PGA), polycaprolactone (PCL), microparticles/microspheres, nanoparticles/nanospheres, and/or liposomes, including any combination thereof. In specific embodiments, a composition comprises an extended time release formulation which comprises PLGA nanoparticles and/or PLGA-PEG nanoparticles.

A composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the composition is preferably in either solid or liquid form, where semi-solid, semi-liquid, suspension and gel forms are included within the forms considered herein as either solid or liquid. Certain embodiments include sterile, injectable solutions.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of an agent such that a suitable dosage will be obtained. Typically, this amount is at least 0.01% of the agent of interest in the composition. When intended for oral administration, this amount may be varied to be between 0.1 and about 70% of the weight of the composition. Certain oral therapeutic or pharmaceutical compositions contain between about 4% and about 75% of the agent of interest. In certain embodiments, therapeutic or pharmaceutical compositions and preparations according to the present invention are prepared so that a parenteral dosage unit contains between 0.01 to 10% by weight of the agent of interest prior to dilution.

The compositions may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a therapeutic or pharmaceutical composition for topical administration.

If intended for transdermal administration, the composition may include a transdermal patch or iontophoresis device.

The compositions may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The therapeutic or pharmaceutical compositions in solid or liquid form may include a component that binds to agent and thereby assists in the delivery of the compound. Suitable components that may act in this capacity include monoclonal or polyclonal antibodies, one or more proteins or a liposome.

The composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The may be prepared by methodology well known in the pharmaceutical art. For example, a composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Administration can be achieved by a variety of different routes, including oral, parenteral, nasal, intravenous, intradermal, intramuscular, subcutaneous or topical. Preferred modes of administration depend upon the nature of the condition to be treated or prevented. Particular embodiments include administration by subcutaneous injection, intravenous (IV) infusion, intradermal injection, intra-tumoral injection, peri-tumoral injection, or intra-lymph node injection, including any combination thereof.

Typical routes of administering these and related therapeutic or vaccine compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Therapeutic or vaccine compositions according to certain embodiments are formulated so as to allow the active ingredients contained therein to be bioavailable upon administration of the composition to a subject or patient.

Compositions that will be administered to a subject or patient may take the form of one or more dosage units, where for example, a tablet may be a single dosage unit, and a container of a herein described agent in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will typically contain a therapeutically effective amount of an agent described herein, for treatment of a disease or condition of interest.

The combination therapies described herein may include administration of a single dosage formulation, which contains a cytokine fusion protein and an autologous tumor cell vaccine and/or an immune checkpoint modulatory agent (optionally with one or more additional active agents), as well as administration of compositions comprising a cytokine fusion protein and an autologous tumor cell vaccine and/or an immune checkpoint modulatory agent, each in its own separate dosage formulation. For example, cytokine fusion protein and an autologous tumor cell vaccine and/or an immune checkpoint modulatory agent can be administered to the subject together in a single IV, parenteral dosage, intra-tumoral, peri-tumoral or other dosage composition such as in a saline solution or other physiologically acceptable solution, or each agent administered in separate dosage formulations. As another example, for cell-based therapies, cytokine fusion protein can be mixed with the cells of an autologous tumor cell vaccine prior to administration, administered as part of a separate composition, or both. Where separate dosage formulations are used, the compositions can be administered at essentially the same time, i.e., concurrently, or at separately staggered times, i.e., sequentially and in any order; combination therapy is understood to include all these regimens.

Also included are patient care kits, comprising one or more fusion proteins, autologous tumor cell vaccines, immune checkpoint modulatory agents, and/or compositions described herein. Certain kits also comprise one or more pharmaceutically-acceptable diluents or solvents, such as water (e.g., sterile water). In some embodiments, the components of the kit are stored in vials, cartridges, dual chamber syringes, and/or pre-filled mixing systems.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

In some embodiments, a patient care kit contains separate containers, dividers, or compartments for the composition(s) and informational material(s). For example, the composition(s) can be contained in a bottle, vial, or syringe, and the informational material(s) can be contained in association with the container. In some embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a cytokine fusion protein and optionally an immune checkpoint modulatory agent. For example, some kits include a plurality of syringes, ampules, foil packets, or blister packs, each containing a single unit dose of a cytokine fusion protein and optionally an immune checkpoint modulatory agent. The containers of the kits can be air tight, waterproof (e.g., impermeable to changes in moisture or evaporation), and/or light-tight.

The patient care kit optionally includes a device suitable for administration of the composition, e.g., a syringe, inhalant, dropper (e.g., eye dropper), swab (e.g., a cotton swab or wooden swab), or any such delivery device. In some embodiments, the device is an implantable device that dispenses metered doses of the agent(s). Also included are methods of providing a kit, e.g., by combining the components described herein.

All publications, patent applications, and issued patents cited in this specification are herein incorporated by reference as if each individual publication, patent application, or issued patent were specifically and individually indicated to be incorporated by reference.

Although the foregoing has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Anti-Tumor Efficacy of the Combination of IL-2 and TNF-α

Recombinant IL-2-TNF-α fusion proteins were developed and their anti-tumor function was tested, alone and in combination with (a) autologous tumor cell lysates, (b) and -PD-1 antibody, and both (a) and (b).

IL-2-TNF-α fusion proteins were prepared according to standard cloning techniques. Mutations were introduced into the native sequences; for human IL-2 (without the signal peptide), the C125S or C125A mutation was introduced to reduce incorrect disulfide-bond formation, and for soluble human TNF-α, the S86T, R31E, and/or R32W mutations were introduced to decrease its specificity activity and affinity to TNFR2. Certain of the constructs are as follows:

(SEQ ID NO: 19)
[ZKBY03] hIL-2(C125S)-(GGGGS)$_3$-hTNF-α (S86T);

(SEQ ID NO: 20)
[ZKBY04A] hIL2(C125A)-(GGGGS)$_2$-hTNF-α (S86T);

```
                                                    (SEQ ID NO: 21)
[ZKBY04B] hIL2(C125A)-(GGGGS)₂-hTNF-α (R32W);

(SEQ ID NO: 22)
[ZKBY05A] hIL2(C125A)-PAPAP-hTNF-α (S86T);

(SEQ ID NO: 23)
[ZKBY05B] hIL2(C125A)-PAPAP-hTNF-α (R32W);

(SEQ ID NO: 24)
[ZKBY06] hIL2(C125A)-PAEAAAKEAAAKA-hTNF-α (S86T);

(SEQ ID NO: 25)
[ZKBY06B] hIL2(C125A)-PAEAAAKEAAAKA-hTNF-α (R32W);
and hIL-2(C125S)-(GGGGS)₃-hTNF-α (R31E, S86T).
```

The IL2-TNF-α fusion protein sequences were designed and the DNA was synthesized. The DNA was sub-cloned into the *E. coli* expression vector pET-32a. The encoded proteins were cloned with an N-terminal His-tag which was later removed during the purification process. The proteins were expressed and purified. One construct (ZKBY04A, also indicated in the Figures as ZKBY04) was selected for further study based on the in vitro activity assay results.

The fusion protein (ZKBY04A) was expressed in *E. coli* as inclusion bodies. The inclusion bodies were dissolved in urea and the protein was purified with Ni column under denatured condition. The protein was then refolded in a refolding buffer containing 50 mM Tris-HCl, 10% glycerol, 150 mM NaCl, and 0.5 M L-Arginine. After the removal of the tag region, the protein was subjected to Ni column again under denatured condition. The protein was refolded and sterilized by filtering. Enterotoxin level in the protein preparation was determined and the protein purity and yield was assayed by SDS-PAGE and Bradford method, respectively. The final product was aliquoted and stored at −80° C. The SDS-PAGE assay for the fusion protein ZKBY04A is shown in FIG. 1.

Activity measurements of IL-2-TNF-α fusion proteins are performed, including a comparison with single agents IL-2 and TNF-α. IL-2 activity is assayed by measuring CTLL-2 cell proliferation.

Figures 2A, 2B:
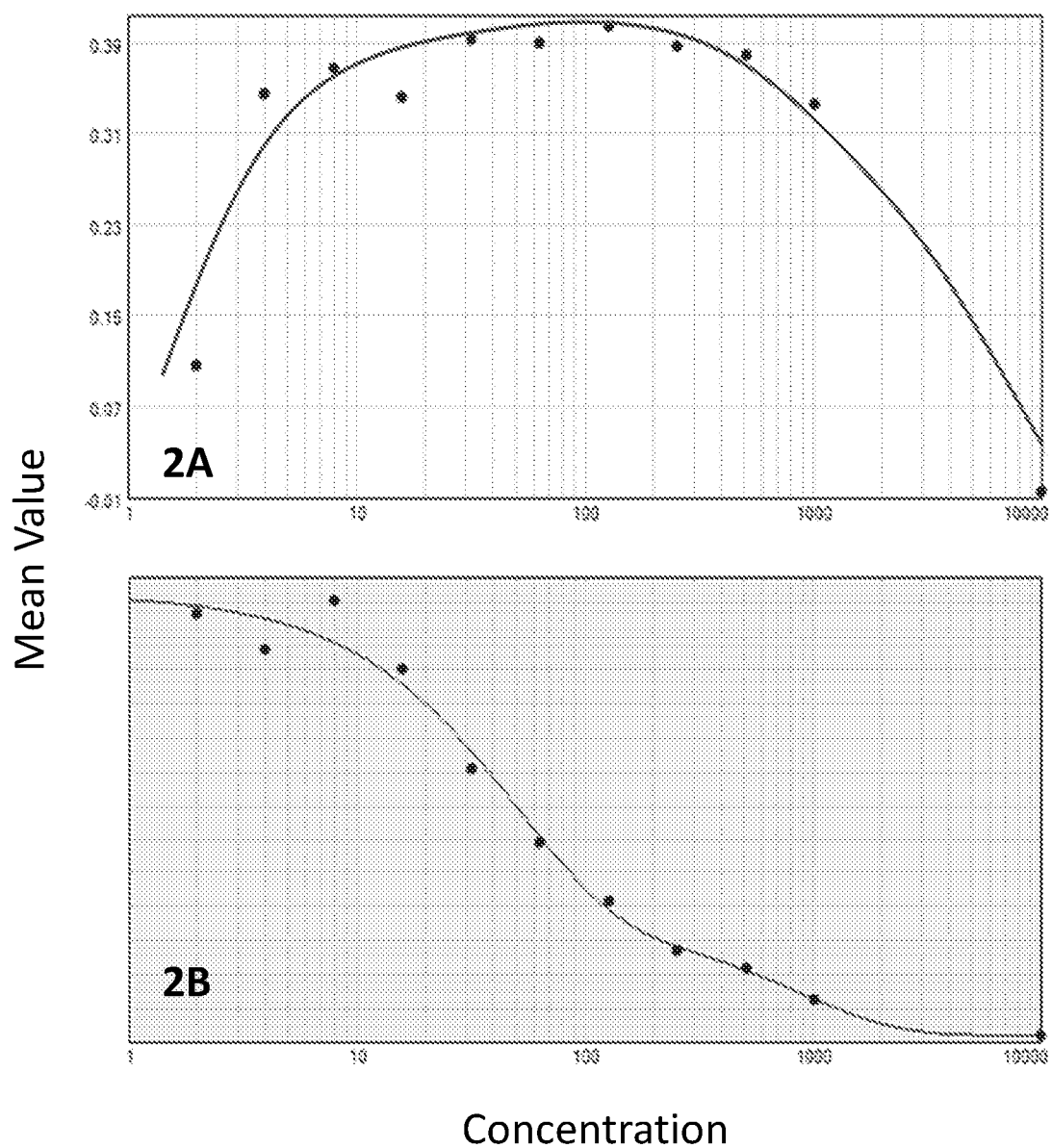
FIGS. 2A-2B show TNF-α activity of test materials assayed by the CCK-8 method in L929 cells.

TNF-α activity of the fusion protein (ZKBY04A) was assayed by the CCK-8 method in L929 cells. Serial dilutions of the ZKBY04A fusion protein were applied to L929 cells and the CCK-8 assay was performed. The data were plotted and the result for protein ZKBY04A showed a more complex response curve in comparison with the sigmoid shaped cure of TNF-α alone. FIG. 2A shows the results for the ZKBY04A fusion protein and FIG. 2B shows the results for commercial TNF-α alone.

Syngeneic mouse models ct-26 and pan-02 are used to test combined effect on tumor growth inhibition by PD-1 antibody and IV-injected IL-2-TNF-α fusion proteins.

Figure 3:
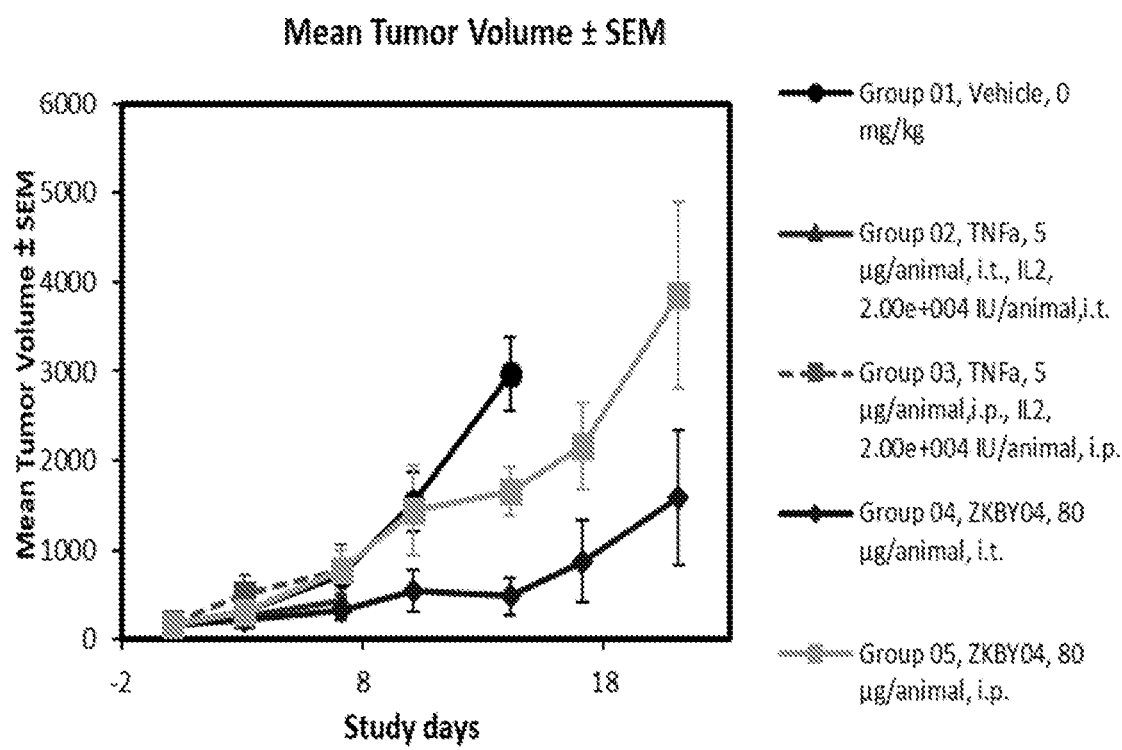
FIG. 3 shows that ZKBY04A has strong anti-tumor effect in the WEHI-164 murine tumor model when injected IT, and a slightly lesser inhibitory effect on tumor growth when injected IP.

The in vivo anti-tumor effect of the IL2-TNF fusion protein ZKBY04A was tested in the WEHI-164 murine tumor model. Soft tissue sarcoma model was generated by implanting WEHI-164 cells into mice (designated as passage 0). When the tumor size reached 150 mm³, the mice were grouped randomly and injected with the drugs either intra-tumorally (IT) or intra-peritoneally (IP). The drugs were injected every three days for a total three times. The tumor size was measured every three days. As shown in FIG. 3, ZKBY04A showed strong anti-tumor effect when injected IT, and a slightly lesser inhibitory effect on tumor growth when injected IP.

Figure 4:
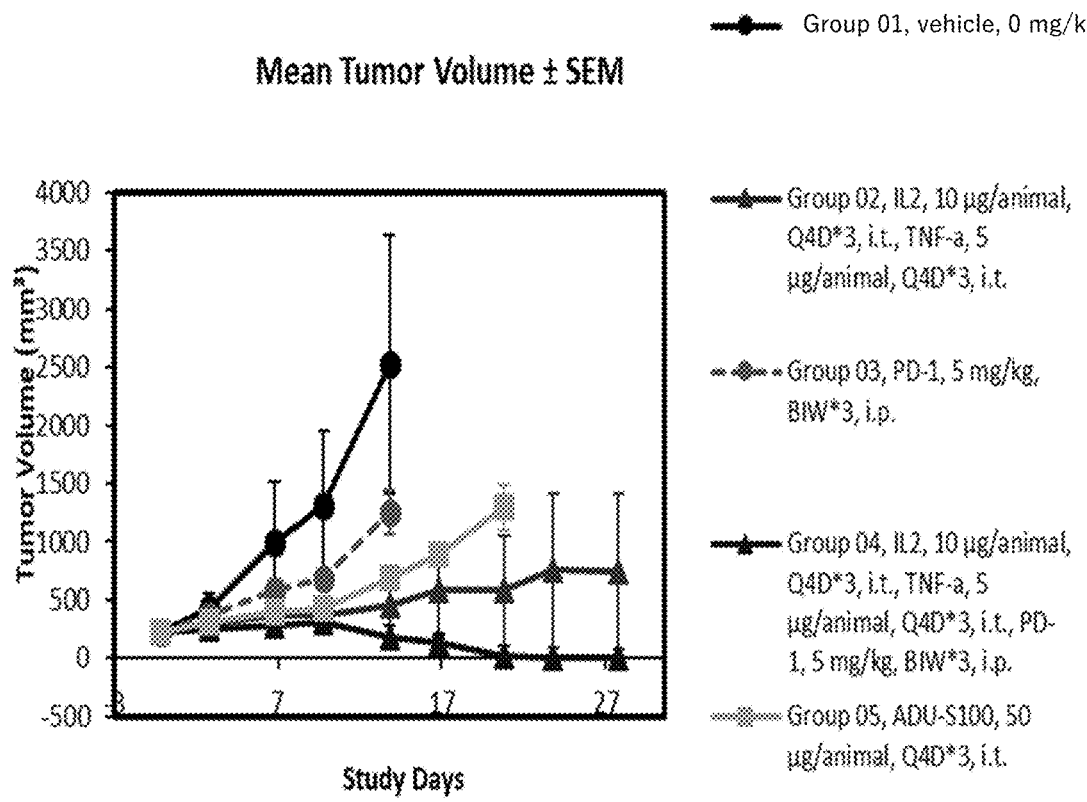
FIG. 4 shows that the combination of IL-2 and TNF-α inhibited tumor growth in the WEHI-164 murine tumor model. The tumor-inhibitory effect was more pronounced when IL-2 and TNF-α were used in combination with a PD-1 antibody.

The in vivo anti-tumor effect of IL-2 and TNF-α was also tested in combination with a PD-1 antibody in the murine tumor model WEHI-164. Similar to above, WEHI-164 mice were injected with PD-1 antibody, the combination of IL-2 and TNF-α, or PD-1 antibody+IL-2+ TNF-α. The STING agonist ADU-S100 was used as comparison. As shown in FIG. 4, the combination of IL-2 and TNF-α showed good inhibition on tumor growth. The effect was more pronounced when IL-2 and TNF-α were used in combination with a PD-1 antibody. The tumors disappeared after 21 days since the first drug treatment in all three mice in the group with IL-2+ TNF-α+PD-1 antibody. One mouse in the group with IL-2+ TNF-α showed tumor disappearance after 31 days.

Figure 5:
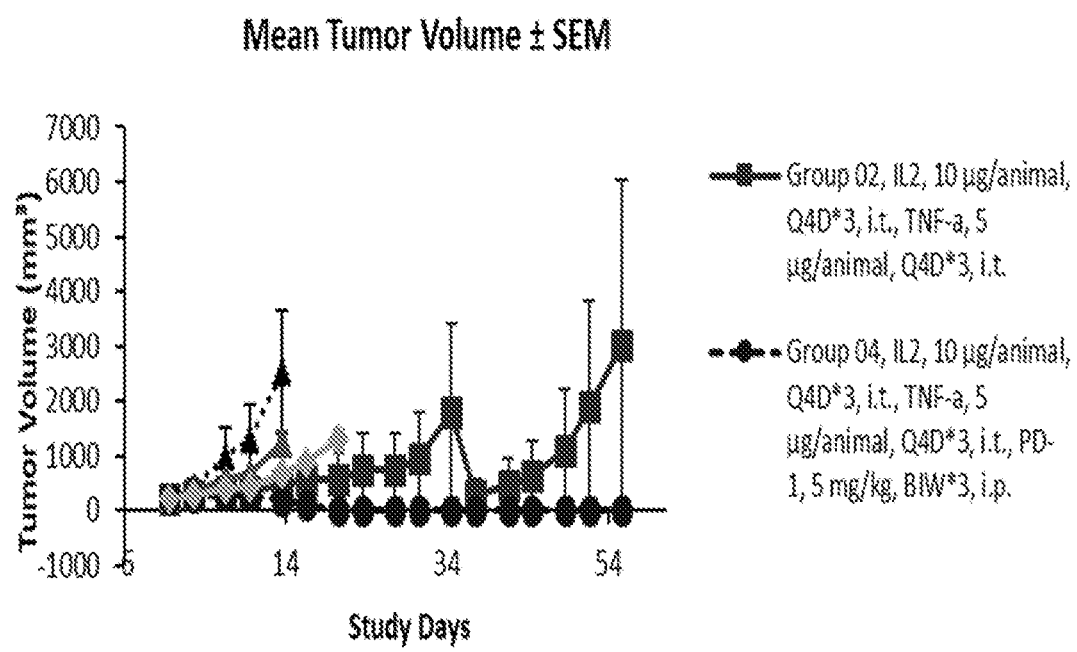
FIG. 5 shows that mice previously cleared of tumor growth did not develop tumors even after being re-challenged with WEHI-164 cells.

The four mice that were cleared of tumor growth were then re-challenged with WEHI-164 cells and kept for three more weeks. As shown in FIG. 5, none of the mice developed tumors, indicating complete cure and the development of immunity or protection against later exposure to the WEHI-164 tumor.

Figures 6A, 6B, 6C:
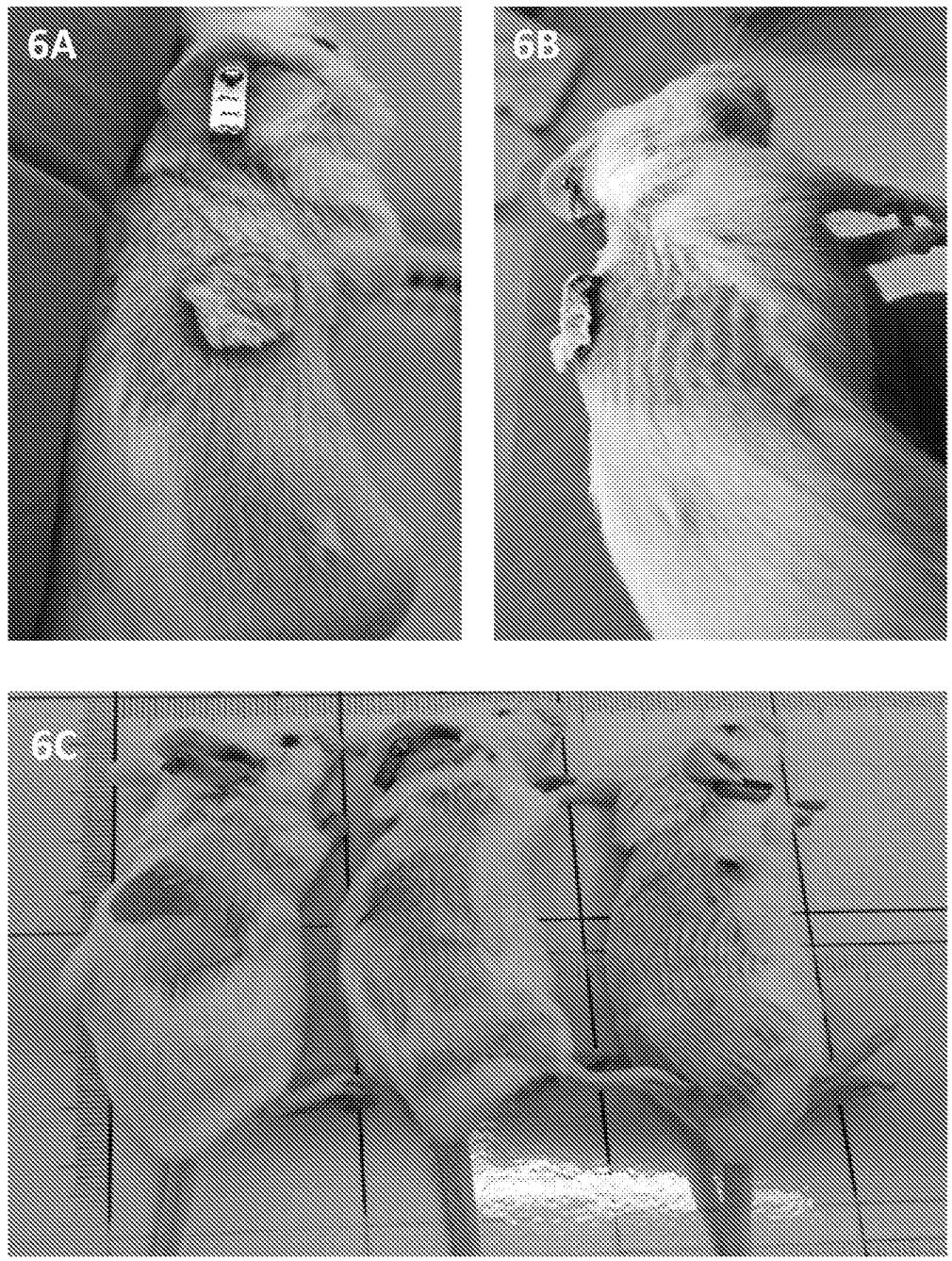
FIGS. 6A-6C show images of the tumors after drug injection for the IL-2+ TNF-α+PD-1 group. Ulceration showed on the tumor a few days after the first injection, and scar tissues later formed at the ulceration sites.
Figure 7:
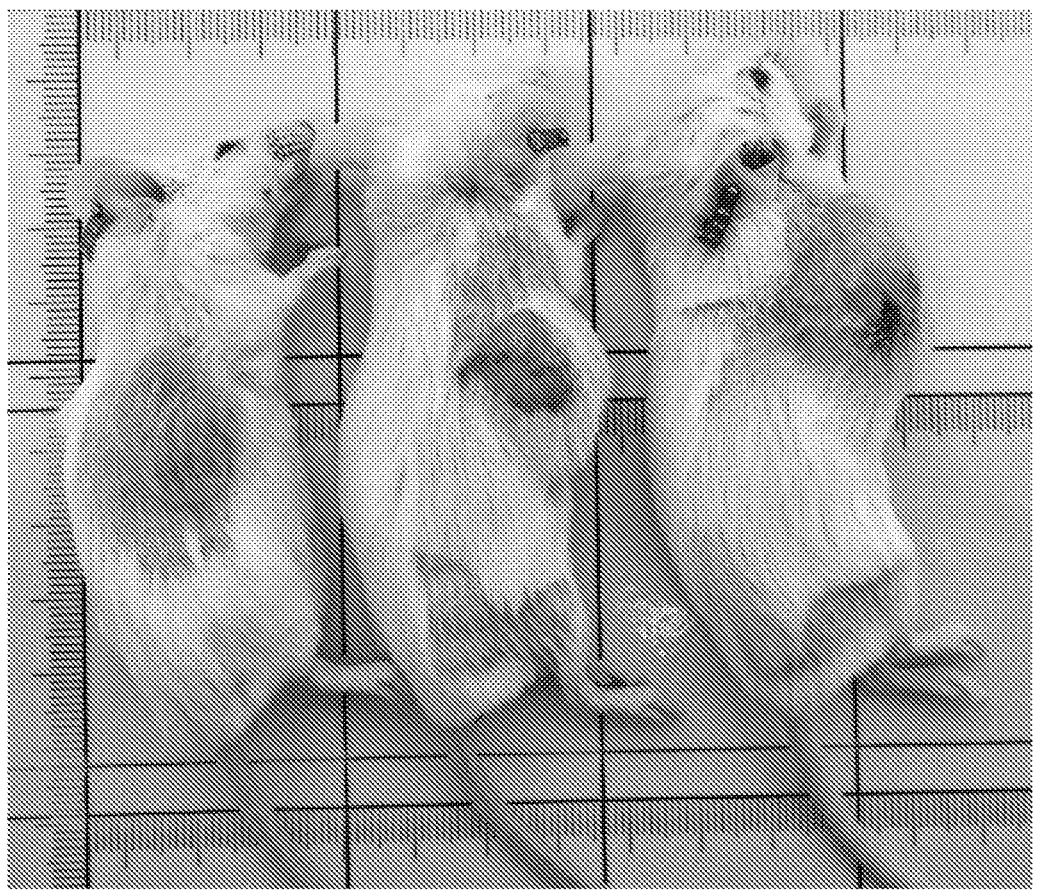
FIG. 7 shows images of the control group, where the tumors grew normally with neither ulceration nor scar formation.

FIGS. 6A-6C show images of the tumors after drug injection for the IL-2+ TNF-α+PD-1 group. Ulceration showed on the tumor a few days after the first injection, and scar tissues later formed at the ulceration sites. Eventually, however, the scars fell off and the mice had no measurable tumors. FIG. 7 shows images of the control group, where the tumors grew normally with neither ulceration nor scar formation.

Figures 8A, 8B:
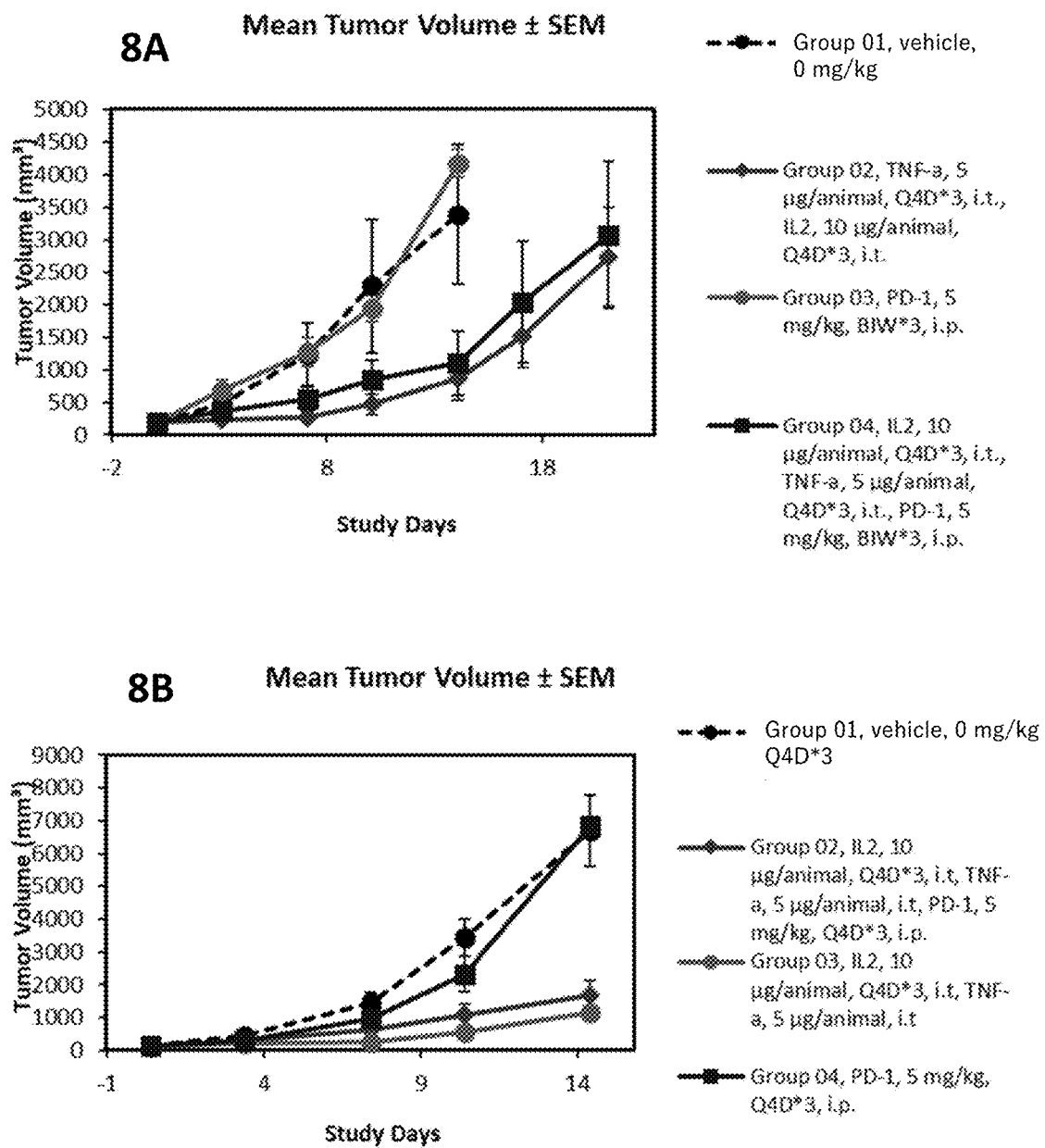
FIGS. 8A-8B show the in vivo anti-tumor effects of the IL-2 and TNF-α combination in the CT26 murine cancer model (8A) and the B16-F10 murine melanoma model (8B).

The in vivo anti-tumor effect of IL-2 and TNF-α was tested in the CT26 murine cancer model and the B16-F10 murine melanoma model. FIG. 8A shows tumor growth inhibition in the CT26 model, and FIG. 8B shows similar tumor growth inhibition in the B16-F10 model.

Drug delivery with PLGA or PLGA-PEG nanoparticles is tested. IL-2-TNF-α fusion proteins are dissolved as a first water phase for double-emulsions. Whole autologous tumor cell lysates+IL-2-TNF-α fusion are also dissolved as first water phase for double-emulsions. Protein levels (total and IL-2-TNF-α) are measured in the PLGA-protein complex: Bradford and ELISA or western-blot.

Tumor whole cell lysates as autologous tumor antigens and formulation of tumor vaccines are also tested in combination with the fusion proteins. Whole cell lysates from tumor cells or tumor tissues are prepared, for example, by encapsulating the lysates with PLGA, together with IL-2-TNF-α fusion proteins to form individualized tumor vaccines. The preparations are lyophilized, and total protein levels are measured.

The separate and combined effects of IL-2-TNF-α fusion proteins, autologous tumor cells lysate, and PD-1 antibodies are tested in syngeneic mouse models, including ct-26, Pan-02, and esophageal tumor models. The mice are injected intravenously, intra-tumorally, and/or peri-tumorally. Dosages and schedules are varied to identify optimal effects, and mechanistic and functional studies are performed, including by IHC and cytokine release analyses.

Example 2

Anti-Tumor Efficacy of the Combination of IFN-β and TNF-α

Figure 9:
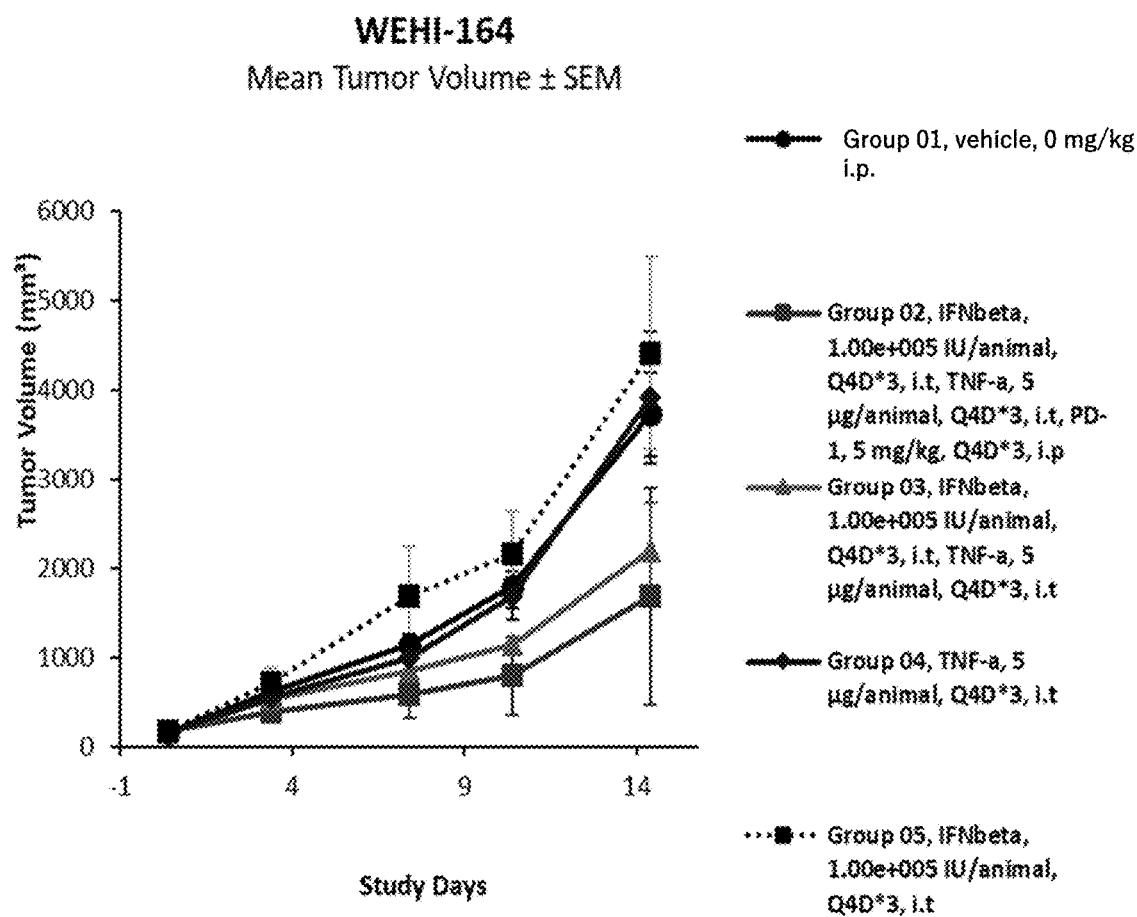
FIG. 9 shows that the combination of IFN-β and TNF-α inhibited tumor growth in the WEHI-164 murine tumor model.
Figures 10A, 10B:
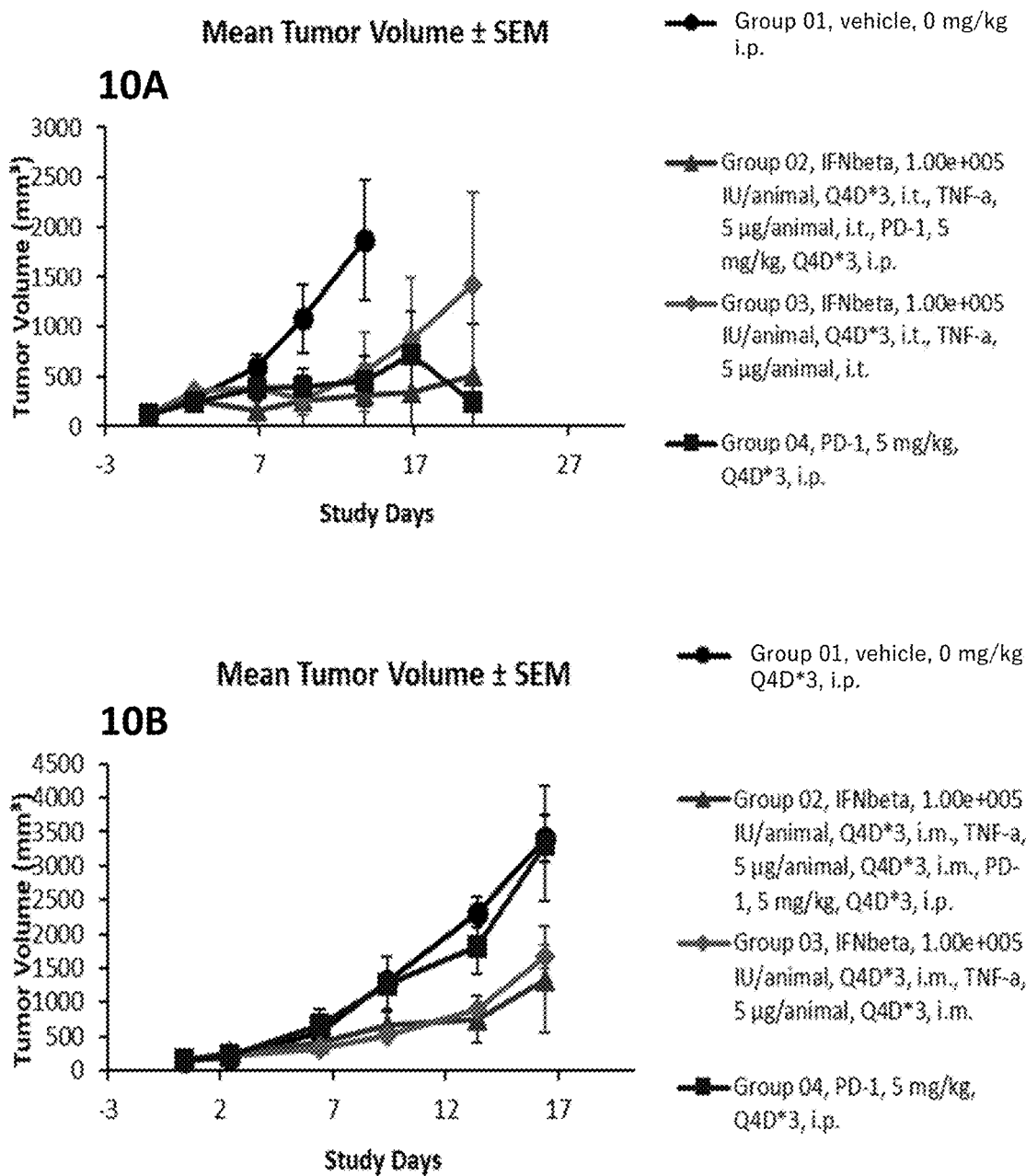
FIGS. 10A-10B show that the combination of IFN-β and TNF-α inhibited tumor growth in the syngeneic Renca murine kidney cancer model (10A) and the CT26 murine colon cancer model (10B).

The in vivo anti-tumor effect of the combination of interferon-β (IFN-β) and TNF-α was initially tested in the WEHI-164 murine tumor model, the syngeneic Renca murine kidney cancer model, and the CT26 murine colon cancer model. FIG. 9 shows tumor growth inhibition in the WEHI-164 model, FIG. 10A shows tumor growth inhibition in the Renca model, and FIG. 10B shows tumor growth inhibition in the CT26 model.

The in vitro activity of an IFN-β-TNF-α fusion protein was tested. Here, an mRNA approach was used to make the fusion protein construct (IFN-β-GGGGS$_2$-TNF-α). The DNA sequence containing full-length human IFN-β, a linker region, and human TNF-α without the signal peptide was designed, synthesized, and cloned into a eukaryotic plasmid vector. The sequence of the construct is shown in Table E1 below.

TABLE E1

| Name | Sequence | SEQ ID NO: |
|---|---|---|
| IFN-β-GGGGS$_2$-TNF-α | ATGACCAACAAGTGTCTCCTCCAAATTGCTC TCCTGTTGTGCTTCTCCACTACAGCTCTTTC CATGAGCTACAACTTGCTTGGATTCCTACAA AGAAGCAGCAATTTTCAGTGTCAGAAGCTCC TGTGGCAATTGAATGGGAGGCTTGAATACTG CCTCAAGGACAGGATGAACTTTGACATCCCT GAGGAGATTAAGCAGCTGCAGCAGTTCCAGA AGGAGGACGCCGCATTGACCATCTATGAGAT GCTCCAGAACATCTTTGCTATTTTCAGACAA GATTCATCTAGCACTGGCTGGAATGAGACTA TTGTTGAGAACCTCCTGGCTAATGTCTATCA TCAGATAAACCATCTGAAGACAGTCCTGGAA GAAAAACTGGAGAAAGAAGATTTCACCAGGG GAAAACTCATGAGCAGTCTGCACCTGAAAAG ATATTATGGAGGATTCTGCATTACCTGAAG GCCAAGGAGTACAGTCACTGTGCCTGGACCA TAGTCAGAGTGGAAATCCTAAGGAACTTTTA CTTCATTAACAGACTTACAGGTTACCTCCGA AACGGTGGCGGTGGCTCTGGAGGGGGAGGGT CCGTCAGATCATCTTCTCGAACCCCGAGTGA | 52 |

TABLE E1-continued

| Name | Sequence | SEQ ID NO: |
|---|---|---|
| | CAAGCCTGTAGCCCATGTTGTAGCAAACCCT CAAGCTGAGGGGCAGCTCCAGTGGCTGAACC GCCGGGCCAATGCCCTCCTGGCCAATGGCGT GGAGCTGAGAGATAACCAGCTGGTGGTGCCA TCAGAGGGCCTGTACCTCATCTACTCCCAGG TCCTCTTCAAGGGCCAAGGCTGCCCCTCCAC CCATGTGCTCCTCACCCACACCATCAGCCGC ATCGCCGTCTCCTACCAGACCAAGGTCAACC TCCTCTCTGCCATCAAGAGCCCCTGCCAGAG GGAGACCCCAGAGGGGGCTGAGGCCAAGCCC TGGTATGAGCCCATCTATCTGGGAGGGGTCT TCCAGCTGGAGAAGGGTGACCGACTCAGCGC TGAGATCAATCGGCCCGACTATCTCGACTTT GCCGAGTCTGGGCAGGTCTACTTTGGGATCA TTGCCCTGTGA | |

PCR was then performed using a pair of primers with an added 3'-polyA tail. The PCR product was used as template for in vitro transcription to make mRNA, a modified 5'-cap, pseudo-UTP and methylated CTP was incorporated for mRNA optimization. The mRNA preparation was transfected into HEK293 cells.

After 24 hour incubation, the medium was collected to test for TNF-α activity by the CCK8 assay in L929 cells, which should indicate production of the secretory fusion protein IFNβ-TNFα. A plasmid containing IFNβ-TNFα was also transfected and TNF-α protein was used as a positive control in the CCK8 assay. FIGS. 11A-11D show that the IFN-β-TNF-α fusion protein has TNF-α activity in the CCK8 assay, whether expressed as a secretory fusion protein from HEK293 cells, or transfected directly into L929 cells.

The invention claimed is:

1. A cytokine fusion protein, comprising a first human cytokine fused to the N-terminus of a second human cytokine, wherein the first cytokine is IL-2 and wherein the second cytokine is TNF-α, wherein the human IL-2 comprises a C125S or C125A mutation and the human TNF-α has increased binding to TNFR1 relative to TNFR2 and B comprises at least one mutation selected from S86T and R32W, including combinations thereof, wherein the first and second cytokines are separated by a stable peptide linker, and wherein the cytokine fusion protein comprises:

(SEQ ID NO: 19)
IL-2(C125S)-(GGGGS)3-TNF-α (S86T);
or (SEQ ID NO: 20)
IL2(C125A)-(GGGGS)2-TNF-α (S86T);

(SEQ ID NO: 21)
IL2(C125A)-(GGGGS)2-TNF-α (R32W);

(SEQ ID NO: 22)
IL2(C125A)-PAPAP-TNF-α (S86T);

(SEQ ID NO: 23)
IL2(C125A)-PAPAP-TNF-α (R32W);

(SEQ ID NO: 24)
IL2(C125A)-PAEAAAKEAAAKA-TNF-α (S86T);

(SEQ ID NO: 25)
IL2(C125A)-PAEAAAKEAAAKA-TNF-α (R32W);

IL-2(C125S)-(GGGGS)3-TNF-α (R31E, S86T);
or (SEQ ID NO: 26)
IFN-β-(GGGGS)2-TNF-α.

an amino acid sequence that is at least 95% identical to a sequence selected from SEQ ID NOs: 19-25 and which has a cytokine signaling activity and anti-tumor activity.

2. The fusion protein of claim 1, comprising, consisting, or consisting essentially of an amino acid sequence selected from SEQ ID NOs: 19-25 and which has a cytokine signaling activity and/or an anti-tumor activity.

3. A method of treating a cancer in a subject in need thereof, comprising administering to the subject a fusion protein of claim 1.

4. The method of claim 3, comprising administering the fusion protein to the subject in combination with an autologous tumor cell vaccine from the subject.

5. The method of claim 4, comprising administering the fusion protein and the autologous tumor vaccine together in the same therapeutic or vaccine composition.

6. The method of claim 5, comprising administering the fusion protein to the subject in combination with an immune checkpoint modulatory agent.

7. The method of claim 6, comprising administering the fusion protein and the immune checkpoint modulatory agent together in the same therapeutic or vaccine composition.

8. The method of claim 3, comprising administering the fusion protein to the subject in combination with an autologous tumor vaccine and an immune checkpoint modulatory agent.

9. The method of claim 8, comprising administering the fusion protein, the autologous tumor vaccine, and the immune checkpoint modulatory agent together in the same therapeutic or vaccine composition.

10. The method of claim 3, wherein the cancer is a primary cancer.

11. The method of claim 3, wherein the cancer is a metastatic cancer.

12. The method of claim 3, wherein the cancer is selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer.

13. The method of claim 11, wherein the metastatic cancer is selected from one or more of:

(a) a bladder cancer which has metastasized to the bone, liver, and/or lungs;

(b) a breast cancer which has metastasized to the bone, brain, liver, and/or lungs;

(c) a colorectal cancer which has metastasized to the liver, lungs, and/or peritoneum;

(d) a kidney cancer which has metastasized to the adrenal glands, bone, brain, liver, and/or lungs;

(e) a lung cancer which has metastasized to the adrenal glands, bone, brain, liver, and/or other lung sites;

(f) a melanoma which has metastasized to the bone, brain, liver, lung, and/or skin/muscle;

(g) a ovarian cancer which has metastasized to the liver, lung, and/or peritoneum;

(h) a pancreatic cancer which has metastasized to the liver, lung, and/or peritoneum;

(i) a prostate cancer which has metastasized to the adrenal glands, bone, liver, and/or lungs;

(j) a stomach cancer which has metastasized to the liver, lung, and/or peritoneum;

(l) a thyroid cancer which has metastasized to the bone, liver, and/or lungs; and (m) a uterine cancer which has metastasized to the bone, liver, lung, peritoneum, and/or vagina.

14. The method of claim 3, comprising administering the fusion protein or therapeutic or vaccine composition by subcutaneous, intravenous, intradermal, intra-tumoral, peritumoral, or intra-lymph node injection, including any combination thereof.

* * * * *

SEQUENCE LISTING

<160> NUMBER OF SEQ ID NOS: 52

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

```
Cys Gln Ser Ile Ile Ser Thr Leu Thr
145                 150

<210> SEQ ID NO 2
<211> LENGTH: 153
<212> TYPE: PRT
<213> ORGANISM: Homo sapiens

<400> SEQUENCE: 2

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Ser Gln Ser Ile Ile Ser Thr Leu Thr
145                 150

<210> SEQ ID NO 3
<211> LENGTH: 233
<212> TYPE: PRT
<213> ORGANISM: Homo sapiens

<400> SEQUENCE: 3

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160
```

```
Val Ser Tyr Gln Thr Lys Val Asn Leu Leu Ser Ala Ile Lys Ser Pro
            165                 170                 175

Cys Gln Arg Glu Thr Pro Glu Gly Ala Glu Ala Lys Pro Trp Tyr Glu
        180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 4
<211> LENGTH: 157
<212> TYPE: PRT
<213> ORGANISM: Homo sapiens

<400> SEQUENCE: 4

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 5
<211> LENGTH: 157
<212> TYPE: PRT
<213> ORGANISM: Homo sapiens

<400> SEQUENCE: 5

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Glu Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95
```

```
Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 6
<211> LENGTH: 157
<212> TYPE: PRT
<213> ORGANISM: Homo sapiens

<400> SEQUENCE: 6

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Thr Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 7
<211> LENGTH: 157
<212> TYPE: PRT
<213> ORGANISM: Homo sapiens

<400> SEQUENCE: 7

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Glu Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Thr Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110
```

```
Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 8
<211> LENGTH: 219
<212> TYPE: PRT
<213> ORGANISM: Homo sapiens

<400> SEQUENCE: 8

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 9
<211> LENGTH: 328
<212> TYPE: PRT
<213> ORGANISM: Homo sapiens

<400> SEQUENCE: 9

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
50                  55                  60
```

```
Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 10
<211> LENGTH: 144
<212> TYPE: PRT
<213> ORGANISM: Homo sapiens

<400> SEQUENCE: 10

Met Trp Leu Gln Ser Leu Leu Leu Leu Gly Thr Val Ala Cys Ser Ile
  1               5                  10                  15

Ser Ala Pro Ala Arg Ser Pro Ser Pro Ser Thr Gln Pro Trp Glu His
             20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110
```

```
Cys Ala Thr Gln Ile Ile Thr Phe Glu Ser Phe Lys Glu Asn Leu Lys
        115                 120                 125

Asp Phe Leu Val Ile Pro Phe Asp Cys Trp Glu Pro Val Gln Glu
    130                 135                 140
```

<210> SEQ ID NO 11
<211> LENGTH: 177
<212> TYPE: PRT
<213> ORGANISM: Homo sapiens

<400> SEQUENCE: 11

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 12
<211> LENGTH: 189
<212> TYPE: PRT
<213> ORGANISM: Homo sapiens

<400> SEQUENCE: 12

```
Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110
```

```
Pro Ser Leu Leu Pro Asp Ser Pro Val Gly Gln Leu His Ala Ser Leu
            115                 120                 125

Leu Gly Leu Ser Gln Leu Leu Gln Pro Glu Gly His His Trp Glu Thr
        130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 13
<211> LENGTH: 243
<212> TYPE: PRT
<213> ORGANISM: Homo sapiens

<400> SEQUENCE: 13

```
Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro
```

<210> SEQ ID NO 14
<211> LENGTH: 229
<212> TYPE: PRT
<213> ORGANISM: Homo sapiens

<400> SEQUENCE: 14

```
Met Thr Pro Gln Leu Leu Leu Ala Leu Val Leu Trp Ala Ser Cys Pro
```

```
              1               5                  10                   15
           Pro Cys Ser Gly Arg Lys Gly Pro Pro Ala Ala Leu Thr Leu Pro Arg
                           20                  25                  30

Val Gln Cys Arg Ala Ser Arg Tyr Pro Ile Ala Val Asp Cys Ser Trp
                           35                  40                  45

Thr Leu Pro Pro Ala Pro Asn Ser Thr Ser Pro Val Ser Phe Ile Ala
                       50                  55                  60

Thr Tyr Arg Leu Gly Met Ala Ala Arg Gly His Ser Trp Pro Cys Leu
           65                      70                  75                  80

Gln Gln Thr Pro Thr Ser Thr Ser Cys Thr Ile Thr Asp Val Gln Leu
                               85                  90                  95

Phe Ser Met Ala Pro Tyr Val Leu Asn Val Thr Ala Val His Pro Trp
                           100                 105                 110

Gly Ser Ser Ser Ser Phe Val Pro Phe Ile Thr Glu His Ile Ile Lys
                           115                 120                 125

Pro Asp Pro Pro Glu Gly Val Arg Leu Ser Pro Leu Ala Glu Arg Gln
           130                     135                 140

Leu Gln Val Gln Trp Glu Pro Pro Gly Ser Trp Pro Phe Pro Glu Ile
           145                     150                 155                 160

Phe Ser Leu Lys Tyr Trp Ile Arg Tyr Lys Arg Gln Gly Ala Ala Arg
                               165                 170                 175

Phe His Arg Val Gly Pro Ile Glu Ala Thr Ser Phe Ile Leu Arg Ala
                           180                 185                 190

Val Arg Pro Arg Ala Arg Tyr Tyr Val Gln Val Ala Ala Gln Asp Leu
                           195                 200                 205

Thr Asp Tyr Gly Glu Leu Ser Asp Trp Ser Leu Pro Ala Thr Ala Thr
                   210                 215                 220

Met Ser Leu Gly Lys
           225

<210> SEQ ID NO 15
<211> LENGTH: 187
<212> TYPE: PRT
<213> ORGANISM: Homo sapiens

<400> SEQUENCE: 15

Met Thr Asn Lys Cys Leu Leu Gln Ile Ala Leu Leu Cys Phe Ser
           1                   5                   10                  15

Thr Thr Ala Leu Ser Met Ser Tyr Asn Leu Leu Gly Phe Leu Gln Arg
                           20                  25                  30

Ser Ser Asn Phe Gln Cys Gln Lys Leu Leu Trp Gln Leu Asn Gly Arg
                           35                  40                  45

Leu Glu Tyr Cys Leu Lys Asp Arg Met Asn Phe Asp Ile Pro Glu Glu
           50                      55                  60

Ile Lys Gln Leu Gln Gln Phe Gln Lys Glu Asp Ala Ala Leu Thr Ile
           65                      70                  75                  80

Tyr Glu Met Leu Gln Asn Ile Phe Ala Ile Phe Arg Gln Asp Ser Ser
                               85                  90                  95

Ser Thr Gly Trp Asn Glu Thr Ile Val Glu Asn Leu Leu Ala Asn Val
                           100                 105                 110

Tyr His Gln Ile Asn His Leu Lys Thr Val Leu Glu Glu Lys Leu Glu
                           115                 120                 125

Lys Glu Asp Phe Thr Arg Gly Lys Leu Met Ser Ser Leu His Leu Lys
           130                     135                 140
```

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 16
<211> LENGTH: 189
<212> TYPE: PRT
<213> ORGANISM: Homo sapiens

<400> SEQUENCE: 16

Met Ala Ser Pro Phe Ala Leu Leu Met Val Leu Val Val Leu Ser Cys
1               5                   10                  15

Lys Ser Ser Cys Ser Leu Gly Cys Asp Leu Pro Glu Thr His Ser Leu
            20                  25                  30

Asp Asn Arg Arg Thr Leu Met Leu Leu Ala Gln Met Ser Arg Ile Ser
        35                  40                  45

Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185

<210> SEQ ID NO 17
<211> LENGTH: 188
<212> TYPE: PRT
<213> ORGANISM: Homo sapiens

<400> SEQUENCE: 17

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Lys Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

```
Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 18
<211> LENGTH: 166
<212> TYPE: PRT
<213> ORGANISM: Homo sapiens

<400> SEQUENCE: 18

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 19
<211> LENGTH: 305
<212> TYPE: PRT
<213> ORGANISM: Artificial Sequence
<220> FEATURE:
<223> OTHER INFORMATION: Made in Lab - IL2(C125S)-(GGGGS)3-TNFalpha
      (S86T) fusion construct

<400> SEQUENCE: 19

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Leu Lys
            50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Gly
130                 135                 140

Gly Gly Ser Val Arg Ser Ser Ser Arg Thr Pro Ser Asp Lys Pro
145                 150                 155                 160

Val Ala His Val Val Ala Asn Pro Gln Ala Glu Gly Gln Leu Gln Trp
                165                 170                 175

Leu Asn Arg Arg Ala Asn Ala Leu Leu Ala Asn Gly Val Glu Leu Arg
            180                 185                 190

Asp Asn Gln Leu Val Val Pro Ser Glu Gly Leu Tyr Leu Ile Tyr Ser
            195                 200                 205

Gln Val Leu Phe Lys Gly Gln Gly Cys Pro Ser Thr His Val Leu Leu
210                 215                 220

Thr His Thr Ile Ser Arg Ile Ala Val Thr Tyr Gln Thr Lys Val Asn
225                 230                 235                 240

Leu Leu Ser Ala Ile Lys Ser Pro Cys Gln Arg Glu Thr Pro Glu Gly
                245                 250                 255

Ala Glu Ala Lys Pro Trp Tyr Glu Pro Ile Tyr Leu Gly Gly Val Phe
            260                 265                 270

Gln Leu Glu Lys Gly Asp Arg Leu Ser Ala Glu Ile Asn Arg Pro Asp
            275                 280                 285

Tyr Leu Asp Phe Ala Glu Ser Gly Gln Val Tyr Phe Gly Ile Ile Ala
            290                 295                 300

Leu
305

<210> SEQ ID NO 20
<211> LENGTH: 300
<212> TYPE: PRT
<213> ORGANISM: Artificial Sequence
<220> FEATURE:
<223> OTHER INFORMATION: Made in Lab - IL2(C125S)-(GGGGS)2-TNFalpha
      (S86T) fusion construct

<400> SEQUENCE: 20

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
            50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr Gly Gly Gly Ser Gly Gly Gly Ser Val
130                 135                 140

Arg Ser Ser Ser Arg Thr Pro Ser Asp Lys Pro Val Ala His Val Val
145                 150                 155                 160

Ala Asn Pro Gln Ala Glu Gly Gln Leu Gln Trp Leu Asn Arg Arg Ala
                165                 170                 175

Asn Ala Leu Leu Ala Asn Gly Val Glu Leu Arg Asp Asn Gln Leu Val
            180                 185                 190

Val Pro Ser Glu Gly Leu Tyr Leu Ile Tyr Ser Gln Val Leu Phe Lys
        195                 200                 205

Gly Gln Gly Cys Pro Ser Thr His Val Leu Leu Thr His Thr Ile Ser
    210                 215                 220

Arg Ile Ala Val Thr Tyr Gln Thr Lys Val Asn Leu Leu Ser Ala Ile
225                 230                 235                 240

Lys Ser Pro Cys Gln Arg Glu Thr Pro Glu Gly Ala Glu Ala Lys Pro
                245                 250                 255

Trp Tyr Glu Pro Ile Tyr Leu Gly Gly Val Phe Gln Leu Glu Lys Gly
            260                 265                 270

Asp Arg Leu Ser Ala Glu Ile Asn Arg Pro Asp Tyr Leu Asp Phe Ala
        275                 280                 285

Glu Ser Gly Gln Val Tyr Phe Gly Ile Ile Ala Leu
    290                 295                 300

<210> SEQ ID NO 21
<211> LENGTH: 300
<212> TYPE: PRT
<213> ORGANISM: Artificial Sequence
<220> FEATURE:
<223> OTHER INFORMATION: Made in Lab - IL2(C125S)-(GGGGS)2-TNFalpha
      (R32W) fusion construct

<400> SEQUENCE: 21

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr Gly Gly Gly Ser Gly Gly Gly Ser Val
130                 135                 140

Arg Ser Ser Ser Arg Thr Pro Ser Asp Lys Pro Val Ala His Val Val
```

```
                145                 150                 155                 160
Ala Asn Pro Gln Ala Glu Gly Gln Leu Gln Trp Leu Asn Arg Trp Ala
                    165                 170                 175

Asn Ala Leu Leu Ala Asn Gly Val Glu Leu Arg Asp Asn Gln Leu Val
                    180                 185                 190

Val Pro Ser Glu Gly Leu Tyr Leu Ile Tyr Ser Gln Val Leu Phe Lys
                    195                 200                 205

Gly Gln Gly Cys Pro Ser Thr His Val Leu Leu Thr His Thr Ile Ser
            210                 215                 220

Arg Ile Ala Val Ser Tyr Gln Thr Lys Val Asn Leu Leu Ser Ala Ile
225                 230                 235                 240

Lys Ser Pro Cys Gln Arg Glu Thr Pro Glu Gly Ala Glu Ala Lys Pro
                    245                 250                 255

Trp Tyr Glu Pro Ile Tyr Leu Gly Gly Val Phe Gln Leu Glu Lys Gly
                    260                 265                 270

Asp Arg Leu Ser Ala Glu Ile Asn Arg Pro Asp Tyr Leu Asp Phe Ala
                    275                 280                 285

Glu Ser Gly Gln Val Tyr Phe Gly Ile Ile Ala Leu
                    290                 295                 300

<210> SEQ ID NO 22
<211> LENGTH: 295
<212> TYPE: PRT
<213> ORGANISM: Artificial Sequence
<220> FEATURE:
<223> OTHER INFORMATION: Made in Lab - IL2(C125S)-PAPAP-TNFalpha (S86T)
      fusion construct

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ph

```
Ser Thr His Val Leu Leu Thr His Thr Ile Ser Arg Ile Ala Val Thr
210                 215                 220

Tyr Gln Thr Lys Val Asn Leu Leu Ser Ala Ile Lys Ser Pro Cys Gln
225                 230                 235                 240

Arg Glu Thr Pro Glu Gly Ala Glu Ala Lys Pro Trp Tyr Glu Pro Ile
                245                 250                 255

Tyr Leu Gly Gly Val Phe Gln Leu Glu Lys Gly Asp Arg Leu Ser Ala
                260                 265                 270

Glu Ile Asn Arg Pro Asp Tyr Leu Asp Phe Ala Glu Ser Gly Gln Val
                275                 280                 285

Tyr Phe Gly Ile Ile Ala Leu
290                 295

<210> SEQ ID NO 23
<211> LENGTH: 295
<212> TYPE: PRT
<213> ORGANISM: Artificial Sequence
<220> FEATURE:
<223> OTHER INFORMATION: Made in Lab - IL2(C125S)-PAPAP-TNFalpha (R32W)
      fusion construct

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Le

-continued

Glu Ile Asn Arg Pro Asp Tyr Leu Asp Phe Ala Glu Ser Gly Gln Val
            275                 280                 285

Tyr Phe Gly Ile Ile Ala Leu
    290                 295

<210> SEQ ID NO 24
<211> LENGTH: 303
<212> TYPE: PRT
<213> ORGANISM: Artificial Sequence
<220> FEATURE:
<223> OTHER INFORMATION: Made in Lab - IL2(C125S)-PAEAAAKEAAAKA-TNFalpha
      (S86T) fusion construct

<400> SEQUENCE: 24

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Pro Ala Glu Ala Ala Ala Lys Glu Ala Ala Ala
    130                 135                 140

Lys Ala Val Arg Ser Ser Ser Arg Thr Pro Ser Asp Lys Pro Val Ala
145                 150                 155                 160

His Val Val Ala Asn Pro Gln Ala Glu Gly Gln Leu Gln Trp Leu Asn
                165                 170                 175

Arg Arg Ala Asn Ala Leu Leu Ala Asn Gly Val Glu Leu Arg Asp Asn
            180                 185                 190

Gln Leu Val Val Pro Ser Glu Gly Leu Tyr Leu Ile Tyr Ser Gln Val
        195                 200                 205

Leu Phe Lys Gly Gln Gly Cys Pro Ser Thr His Val Leu Leu Thr His
    210                 215                 220

Thr Ile Ser Arg Ile Ala Val Thr Tyr Gln Thr Lys Val Asn Leu Leu
225                 230                 235                 240

Ser Ala Ile Lys Ser Pro Cys Gln Arg Glu Thr Pro Glu Gly Ala Glu
                245                 250                 255

Ala Lys Pro Trp Tyr Glu Pro Ile Tyr Leu Gly Gly Val Phe Gln Leu
            260                 265                 270

Glu Lys Gly Asp Arg Leu Ser Ala Glu Ile Asn Arg Pro Asp Tyr Leu
        275                 280                 285

Asp Phe Ala Glu Ser Gly Gln Val Tyr Phe Gly Ile Ile Ala Leu
    290                 295                 300

<210> SEQ ID NO 25
<211> LENGTH: 303
<212> TYPE: PRT

<213> ORGANISM: Artificial Sequence
<220> FEATURE:
<223> OTHER INFORMATION: Made in Lab - IL2(C125S)-PAEAAAKEAAAKA-TNFalpha
      (R32W) fusion construct

<400> SEQUENCE: 25

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Pro Ala Glu Ala Ala Ala Lys Glu Ala Ala Ala
130                 135                 140

Lys Ala Val Arg Ser Ser Arg Thr Pro Ser Asp Lys Pro Val Ala
145                 150                 155                 160

His Val Val Ala Asn Pro Gln Ala Glu Gly Gln Leu Gln Trp Leu Asn
                165                 170                 175

Arg Trp Ala Asn Ala Leu Leu Ala Asn Gly Val Glu Leu Arg Asp Asn
            180                 185                 190

Gln Leu Val Val Pro Ser Glu Gly Leu Tyr Leu Ile Tyr Ser Gln Val
        195                 200                 205

Leu Phe Lys Gly Gln Gly Cys Pro Ser Thr His Val Leu Leu Thr His
210                 215                 220

Thr Ile Ser Arg Ile Ala Val Ser Tyr Gln Thr Lys Val Asn Leu Leu
225                 230                 235                 240

Ser Ala Ile Lys Ser Pro Cys Gln Arg Glu Thr Pro Glu Gly Ala Glu
                245                 250                 255

Ala Lys Pro Trp Tyr Glu Pro Ile Tyr Leu Gly Gly Val Phe Gln Leu
            260                 265                 270

Glu Lys Gly Asp Arg Leu Ser Ala Glu Ile Asn Arg Pro Asp Tyr Leu
        275                 280                 285

Asp Phe Ala Glu Ser Gly Gln Val Tyr Phe Gly Ile Ile Ala Leu
    290                 295                 300
```

<210> SEQ ID NO 26
<211> LENGTH: 353
<212> TYPE: PRT
<213> ORGANISM: Artificial Sequence
<220> FEATURE:
<223> OTHER INFORMATION: Made in Lab - IFNbeta-GGGGS2-TNFalpha fusion
      construct

<400> SEQUENCE: 26

```
Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
```

```
            20                  25                  30
Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
                100                 105                 110

Tyr His Gln Ile Asn His Leu Lys Thr Val Leu Glu Glu Lys Leu Glu
                115                 120                 125

Lys Glu Asp Phe Thr Arg Gly Lys Leu Met Ser Ser Leu His Leu Lys
                130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Gly Gly Gly Gly Ser
                180                 185                 190

Gly Gly Gly Gly Ser Val Arg Ser Ser Arg Thr Pro Ser Asp Lys
                195                 200                 205

Pro Val Ala His Val Val Ala Asn Pro Gln Ala Glu Gly Gln Leu Gln
                210                 215                 220

Trp Leu Asn Arg Arg Ala Asn Ala Leu Leu Ala Asn Gly Val Glu Leu
225                 230                 235                 240

Arg Asp Asn Gln Leu Val Val Pro Ser Glu Gly Leu Tyr Leu Ile Tyr
                245                 250                 255

Ser Gln Val Leu Phe Lys Gly Gln Gly Cys Pro Ser Thr His Leu Leu
                260                 265                 270

Thr His Thr Ile Ser Arg Ile Ala Val Ser Tyr Gln Thr Lys Val Asn
                275                 280                 285

Leu Leu Ser Ala Ile Lys Ser Pro Cys Gln Arg Glu Thr Pro Glu Gly
                290                 295                 300

Ala Glu Ala Lys Pro Trp Tyr Glu Pro Ile Tyr Leu Gly Gly Val Phe
305                 310                 315                 320

Gln Leu Glu Lys Gly Asp Arg Leu Ser Ala Glu Ile Asn Arg Pro Asp
                325                 330                 335

Tyr Leu Asp Phe Ala Glu Ser Gly Gln Val Tyr Phe Gly Ile Ile Ala
                340                 345                 350

Leu

<210> SEQ ID NO 27
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 27

Gly Ser Gly Ser
1

<210> SEQ ID NO 28
```

```
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 28

Gly Gly Ser Gly
1

<210> SEQ ID NO 29
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 29

Gly Gly Gly Ser
1

<210> SEQ ID NO 30
<211> LENGTH: 5
<212> TYPE: PRT
<213> ORGANISM: Artificial Sequence
<220> FEATURE:
<223> OTHER INFORMATION: Synthesized peptide linker

<400> SEQUENCE: 30

Gly Gly Gly Gly Ser
1               5

<210> SEQ ID NO 31
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 31

Gly Asn Gly Asn
1

<210> SEQ ID NO 32
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 32

Gly Gly Asn Gly
1

<210> SEQ ID NO 33
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 33

Gly Gly Gly Asn
1

<210> SEQ ID NO 34
<211> LENGTH: 5
```

```
<212> TYPE: PRT
<213> ORGANISM: Artificial Sequence
<220> FEATURE:
<223> OTHER INFORMATION: Synthesized peptide linker

<400> SEQUENCE: 34

Gly Gly Gly Gly Asn
1               5

<210> SEQ ID NO 35
<211> LENGTH: 7
<212> TYPE: PRT
<213> ORGANISM: Artificial Sequence
<220> FEATURE:
<223> OTHER INFORMATION: Synthesized peptide linker

<400> SEQUENCE: 35

Ala Glu Ala Ala Ala Lys Ala
1               5

<210> SEQ ID NO 36
<211> LENGTH: 12
<212> TYPE: PRT
<213> ORGANISM: Artificial Sequence
<220> FEATURE:
<223> OTHER INFORMATION: Synthesized peptide linker

<400> SEQUENCE: 36

Ala Glu Ala Ala Ala Lys Glu Ala Ala Ala Lys Ala
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Synthesized peptide linker

<400> SEQUENCE: 37

Ala Pro Ala Pro Lys Pro
1               5

<210> SEQ ID NO 38
<211> LENGTH: 12
<212> TYPE: PRT
<213> ORGANISM: Artificial Sequence
<220> FEATURE:
<223> OTHER INFORMATION: Synthesized peptide linker

<400> SEQUENCE: 38

Ala Pro Ala Pro Lys Pro Glu Pro Ala Pro Lys Pro
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthesized peptide linker

<400> SEQUENCE: 39

Gly Gly Gly Gly Ser Gly Gly Gly Gly Ser
1               5                   10

<210> SEQ ID NO 40
<211> LENGTH: 5
<212> TYPE: PRT
```

```
<213> ORGANISM: Artificial Sequence
<220> FEATURE:
<223> OTHER INFORMATION: Synthesized peptide linker

<400> SEQUENCE: 40

Asp Gly Gly Gly Ser
1               5

<210> SEQ ID NO 41
<211> LENGTH: 5
<212> TYPE: PRT
<213> ORGANISM: Artificial Sequence
<220> FEATURE:
<223> OTHER INFORMATION: Synthesized peptide linker

<400> SEQUENCE: 41

Thr Gly Glu Lys Pro
1               5

<210> SEQ ID NO 42
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 42

Gly Gly Arg Arg
1

<210> SEQ ID NO 43
<211> LENGTH: 14
<212> TYPE: PRT
<213> ORGANISM: Artificial Sequence
<220> FEATURE:
<223> OTHER INFORMATION: Synthesized peptide linker

<400> SEQUENCE: 43

Glu Gly Lys Ser Ser Gly Ser Gly Ser Glu Ser Lys Val Asp
1               5                   10

<210> SEQ ID NO 44
<211> LENGTH: 18
<212> TYPE: PRT
<213> ORGANISM: Artificial Sequence
<220> FEATURE:
<223> OTHER INFORMATION: Synthesized peptide linker

<400> SEQUENCE: 44

Lys Glu Ser Gly Ser Val Ser Ser Glu Gln Leu Ala Gln Phe Arg Ser
1               5                   10                  15

Leu Asp

<210> SEQ ID NO 45
<211> LENGTH: 8
<212> TYPE: PRT
<213> ORGANISM: Artificial Sequence
<220> FEATURE:
<223> OTHER INFORMATION: Synthesized peptide linker

<400> SEQUENCE: 45

Gly Gly Arg Arg Gly Gly Gly Ser
1               5

<210> SEQ ID NO 46
<211> LENGTH: 9
```

```
<212> TYPE: PRT
<213> ORGANISM: Artificial Sequence
<220> FEATURE:
<223> OTHER INFORMATION: Synthesized peptide linker

<400> SEQUENCE: 46

Leu Arg Gln Arg Asp Gly Glu Arg Pro
1               5

<210> SEQ ID NO 47
<211> LENGTH: 12
<212> TYPE: PRT
<213> ORGANISM: Artificial Sequence
<220> FEATURE:
<223> OTHER INFORMATION: Synthesized peptide linker

<400> SEQUENCE: 47

Leu Arg Gln Lys Asp Gly Gly Gly Ser Glu Arg Pro
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Synthesized peptide linker

<400> SEQUENCE: 48

Leu Arg Gln Lys Asp Gly Gly Gly Ser Gly Gly Gly Ser Glu Arg Pro
1               5                   10                  15

<210> SEQ ID NO 49
<211> LENGTH: 5
<212> TYPE: PRT
<213> ORGANISM: Artificial Sequence
<220> FEATURE:
<223> OTHER INFORMATION: Synthesized peptide linker

<400> SEQUENCE: 49

Pro Ala Pro Ala Pro
1               5

<210> SEQ ID NO 50
<211> LENGTH: 13
<212> TYPE: PRT
<213> ORGANISM: Artificial Sequence
<220> FEATURE:
<223> OTHER INFORMATION: Synthesized peptide linker

<400> SEQUENCE: 50

Pro Ala Glu Ala Ala Ala Lys Glu Ala Ala Ala Lys Ala
1               5                   10

<210> SEQ ID NO 51
<211> LENGTH: 10
<212> TYPE: DNA
<213> ORGANISM: Artificial Sequence
<220> FEATURE:
<223> OTHER INFORMATION: Kozak consensus sequence

<400> SEQUENCE: 51 rccrccatgg                                                              10

<210> SEQ ID NO 52
<211> LENGTH: 1065
<212> TYPE: DNA
<213> ORGANISM: Artificial Sequence
```

<220> FEATURE:
<223> OTHER INFORMATION: Made in Lab - mRNA for IFNbeta-GGGGS2-TNFalpha fusion construct

<400> SEQUENCE: 52

```
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tactgcctca aggacaggat gaactttgac     180
atccctgagg agattaagca gctgcagcag ttccagaagg aggacgccgc attgaccatc     240
tatgagatgc tccagaacat ctttgctatt ttcagacaag attcatctag cactggctgg     300
aatgagacta ttgttgagaa cctcctggct aatgtctatc atcagataaa ccatctgaag     360
acagtcctgg aagaaaaact ggagaaagaa gatttcacca ggggaaaact catgagcagt     420
ctgcacctga aaagatatta tgggaggatt ctgcattacc tgaaggccaa ggagtacagt     480
cactgtgcct ggaccatagt cagagtggaa atcctaagga acttttactt cattaacaga     540
cttacaggtt acctccgaaa cggtggcggt ggctctggag gggagggtc cgtcagatca      600
tcttctcgaa ccccgagtga caagcctgta gcccatgttg tagcaaaccc tcaagctgag     660
gggcagctcc agtggctgaa ccgccgggcc aatgccctcc tggccaatgg cgtggagctg     720
agagataacc agctggtggt gccatcagag ggcctgtacc tcatctactc ccaggtcctc     780
ttcaagggcc aaggctgccc ctccacccat gtgctcctca cccacaccat cagccgcatc     840
gccgtctcct accagaccaa ggtcaacctc ctctctgcca tcaagagccc ctgccagagg     900
gagccccag aggggctga ggccaagccc tggtatgagc ccatctatct gggaggggtc        960
ttccagctgg agaagggtga ccgactcagc gctgagatca atcggcccga ctatctcgac     1020
tttgccgagt ctgggcaggt ctactttggg atcattgccc tgtga                     1065
```